(12) United States Patent
Kawai et al.

(10) Patent No.: US 8,058,286 B2
(45) Date of Patent: Nov. 15, 2011

(54) METHOD FOR THERAPY OF DIARRHEA-PREDOMINANT IRRITABLE BOWEL DISORDERS

(75) Inventors: Koji Kawai, Kanagawa (JP); Morihiro Fujimura, Kanagawa (JP); Sayoko Kanie, Fujisawa (JP); Yohei Noro, Otsu (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 12/084,633

(22) PCT Filed: Nov. 7, 2006

(86) PCT No.: PCT/JP2006/322134

§ 371 (c)(1),
(2), (4) Date: Jun. 19, 2008

(87) PCT Pub. No.: WO2007/055184

PCT Pub. Date: May 18, 2007

(65) Prior Publication Data

US 2009/0111843 A1    Apr. 30, 2009

(30) Foreign Application Priority Data

Nov. 9, 2005  (JP) .................................. 2005-324365

(51) Int. Cl.
*A61K 321/485*    (2006.01)
(52) U.S. Cl. ........................................ 514/282
(58) Field of Classification Search ................. None
See application file for complete search history.

(56) References Cited

U.S. PATENT DOCUMENTS

| | | | |
|---|---|---|---|
| 4,987,136 A | 1/1991 | Kreek et al. | |
| 6,174,891 B1 | 1/2001 | Nagase et al. | |
| 7,320,984 B2 * | 1/2008 | Izumimoto et al. | 514/282 |
| 2004/0122230 A1 | 6/2004 | Welsh et al. | |
| 2005/0038061 A1 | 2/2005 | Schutz et al. | |

FOREIGN PATENT DOCUMENTS

| | | |
|---|---|---|
| EP | 1 555 266 A1 | 7/2005 |
| WO | WO-83/03197 A1 | 9/1983 |
| WO | WO-98/23290 A1 | 6/1998 |
| WO | WO-2005/094826 A1 | 10/2005 |
| WO | WO-2006/049248 A1 | 5/2006 |

OTHER PUBLICATIONS

The Merck Manual, 17th edition (1999), p. 312.*
Berman et al., Journal Neurosci.. 28(2) (Jan. 2008), pp. 349-359.*
Ness, T.J., ILAR Journal,V40(3) (1999).*
Kohn et al., Selected aspects of the clinical pharmacology of visceral analgesics and gut motility modifying drugs in the horse, Journal of Veterinary Internal Medicine, vol. 12, No. 2, Apr.-Jun. 1998, pp. 85-91, Abstract.*
Supplementary European Search Report—PCT/JP2006322134, dated Mar. 28, 2011.

* cited by examiner

*Primary Examiner* — Phyllis G. Spivack
(74) *Attorney, Agent, or Firm* — Birch, Stewart, Kolasch and Birch, LLP

(57) ABSTRACT

A method for therapy of diarrhea-predominant irritable bowel disorders comprising as an effective ingredient a morphinan derivative having a nitrogen-containing cyclic group or a pharmaceutically acceptable acid addition salt thereof is disclosed. The method for therapy of diarrhea-predominant irritable bowel disorders comprises as an effective ingredient a morphinan derivative or a pharmaceutically acceptable acid addition salt thereof, having a specific structure, such as N-(17-cyclopeopylmethyl-4,5α-epoxy-3,14-dihydroxy-morphinan-6β-yl)-3,4,5,6-tetrahydrophthalimide tartaric acid salt (Compound 10).

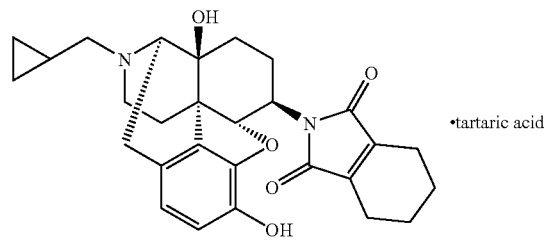

1 Claim, No Drawings

METHOD FOR THERAPY OF DIARRHEA-PREDOMINANT IRRITABLE BOWEL DISORDERS

TECHNICAL FIELD

The present invention relates to a therapeutic or prophylactic agent for functional bowel disorders, comprising as an effective ingredient a morphinan derivative having a nitrogen-containing cyclic substituent or a pharmaceutically acceptable acid addition salt thereof, which is useful for therapy or prophylaxis of functional bowel disorders, particularly irritable bowel syndrome.

BACKGROUND ART

According to Rome II which are diagnostic criteria of the entire functional gastrointestinal disorders, "the state in which lower gastrointestinal tract symptoms are observed, but an organic disease is not found" is diagnosed as a functional bowel disorder. The functional bowel disorders having characteristic syndromes are subclassified into irritable bowel syndrome (IBS), functional diarrhea, functional constipation and functional abdominal distension. Functional diarrhea is a group of diseases whose main symptom is chronic diarrhea without abdominal pain. Functional constipation is a group of diseases whose main symptom is chronic constipation without abdominal pain. Functional abdominal distension is a group of diseases whose main symptoms are abdominal distension and gas, in which abdominal pain is not predominant. Irritable bowel syndrome are diseases which are not classified into any of the functional diarrhea, functional constipation and functional abdominal distension, and may be thought to be a generic name of diarrheal diseases with abdominal pain (diarrheal IBS), costive diseases with abdominal pain (costive IBS) and diseases in which diarrhea and constipation both with abdominal pain alternately appear (alternating IBS).

In the diarrheal IBS, frequent diarrhea in a small amount continues for a long time. Against this symptom, to inhibit contraction of smooth muscle, an anticholinergic drug with antispasmodic property is often used, and a drug for controlling intestinal function is often used in combination. Costive IBS is a spastic constipation caused by enhanced movement of intestinal tract. Against this symptom, a method in which the hardness of feces is controlled by using a saline purgative is often employed. In alternating IBS, diarrhea and constipation alternate with time, and it is difficult to cure this disease with a drug, but basically, a gastrointestinal motility improvement agent is used for alleviating the symptom. However, up to now, a curative drug for irritable bowel syndrome does not exist, and merely symptomatic treatments for the purpose of alleviation of each type of symptoms are performed.

In the meantime, as for the therapeutic effect of the compounds having morphinan skeleton against functional bowel disorders, especially irritable bowel syndrome, a low dosage prescription of naltrexone which is an opioid receptor antagonist has been disclosed (Patent Literature 1). Although data showing pharmacological effects are not shown, it has been suggested that a group of compounds including a specific 6-amino substituted morphinan derivative may be applied to bowel diseases (Patent Literatures 2 and 3). Further, it has been reported that loperamide (Non-Patent Literature 1) which is an opioid agonist, and fedotozine which is a peripheral opioid κ agonist are effective for irritable bowel syndrome, although these compounds have no structural similarity with the compounds contained in the agent according to the present invention.

On the other hand, it has been disclosed that morphinan derivatives having a nitrogen-containing cyclic substituent at 6-position used in the present invention are useful as a therapeutic or prophylactic agent for frequent urination or urinary incontinence, as an antipruritic, or as an analgesic (Patent Literatures 4, 5 and 6. The use as an analgesic was disclosed after the priority date of the present application). It has also been reported that morphinan derivatives including those having a nitrogen-containing cyclic substituent at 6-position are useful as an analgesic, diuretic, antitussive, and as a brain cell-protecting agent (Patent Literature 7). Further, some references (Patent Literatures 8 and 9, Non-Patent Literatures 3, 4 and 5) report that morphinan derivatives having a nitrogen-containing cyclic substituent included in those used in the present invention, none of the references suggest the effect against the functional bowel disorders.

There is no relationship between the structures of the compounds disclosed in the above-described prior art references as well as their pharmacological effects through the opioid receptor and the effects of the compounds used in the present invention against the functional bowel disorders. Thus, these references do not infer at all the significant and useful therapeutic or prophylactic effect of the compounds characterized by having a nitrogen-containing cyclic substituent at the 6-position of the morphinan structure.

Patent Literature 1: International Publication WO 00/051592

Patent Literature 2: International Publication WO 03/051888

Patent Literature 3: International Publication WO 02/036573

Patent Literature 4: International Publication WO 04/033457

Patent Literature 5: International Publication WO 05/094826

Patent Literature 6: International Publication WO 06/049248

Patent Literature 7: International Publication WO 95/03308

Patent Literature 8: Japanese Patent Publication (Kokoku) No. 41-18824

Patent Literature 9: Japanese Patent Publication (Kokoku) No. 41-18826

Non-Patent Literature 1: Talley N. J., Am. J. Gastroenterol, 98(4), 750-8, 2003.

Non-Patent Literature 2: Dapoigny M. et. al., Dig. Dis. Sci., 40(10), 2244-9, 1995.

Non-Patent Literature 3: Simon C. et. al., Tetrahedron, 50, 9757, 1994.

Non-Patent Literature 4: Sayre L. M. et. al., J. Med. Chem., 27, 1325, 1984.

Non-Patent Literature 5: Simon C. et. al., Synth. Commun., 22, 913, 1992.

DISCLOSURE OF THE INVENTION

Problems which the Invention Tries to Solve

An object of the present invention is to provide a therapeutic or prophylactic agent for functional bowel disorders, comprising as an effective ingredient a morphinan derivative having a nitrogen-containing cyclic substituent or a pharmaceutically acceptable acid addition salt thereof, which is useful for therapy or prophylaxis of functional bowel disorders, particularly irritable bowel syndrome.

Means for Solving the Problems

The present inventors intensively studied for attaining the above-described object to discover that the compounds having a nitrogen-containing cyclic substituent on a specific position of the morphinan structure have excellent therapeutic effects against functional bowel disorders and the side effects thereof are small, thereby completing the present invention.

That is, the present invention provides a therapeutic or prophylactic agent for functional bowel disorders comprising as an effective ingredient a morphinan derivative having a nitrogen-containing cyclic substituent of the Formula (I):

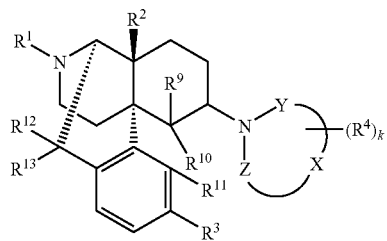

[wherein $R^1$ is hydrogen, $C_1$-$C_5$ alkyl, $C_4$-$C_7$ cycloalkylalkyl, $C_5$-$C_8$ cycloalkenylalkyl, $C_6$-$C_{12}$ aryl, $C_7$-$C_{13}$ aralkyl, $C_3$-$C_7$ alkenyl, furanylalkyl (wherein the number of carbon atoms in the alkyl moiety is 1 to 5), thienylalkyl (wherein the number of carbon atoms in the alkyl moiety is 1 to 5) or pyridylalkyl (wherein the number of carbon atoms in the alkyl moiety is 1 to 5);

$R^2$ and $R^3$ are independently hydrogen, hydroxy, $C_1$-$C_5$ alkoxy, $C_3$-$C_7$ alkenyloxy, $C_7$-$C_{13}$ aralkyloxy or $C_1$-$C_5$ alkanoyloxy;

Y and Z independently represent valence bond or —C(=O)—;

—X— represents $C_2$-$C_7$ alkylene, alkenylene or alkynylene (one or more of the carbon atoms therein may be replaced by (a) nitrogen, oxygen or sulfur atom(s)) constituting a part of the ring structure;

k is an integer of 0 to 8;

$R^4$ is(are) (a) substituent(s) in the number of k on the nitrogen-containing ring, which independently represent(s) fluorine, chlorine, bromine, iodine, nitro, $C_1$-$C_5$ alkyl, $C_1$-$C_5$ alkylidene, $C_7$-$C_{13}$ cycloalkylalkyl, $C_6$-$C_{12}$ aryl, $C_7$-$C_{13}$ aralkyl, $C_7$-$C_{13}$ aralkylidene, trifluoromethyl, trifluoromethoxy, cyano, isothiocyanato, $(CH_2)_p SR^6$, $(CH_2)_p S(O)R^6$, $(CH_2)_p S(O_2)R^6$, $(CH_2)_p OR^6$, $(CH_2)_p C(=O)R^6$, $(CH_2)_p OC(=O)R^6$, $(CH_2)_p CO_2 R^6$, $(CH_2)_p S(O_2)NR^7 R^8$, $(CH_2)_p C(=O)NR^7 R^8$, $(CH_2)_p NR^7 R^8$, $(CH_2)_p N(R^7)C(=O)R^8$, $(CH_2)_p N(R^7)S(O_2)R^8$, or among the $R^4$s in the number of k, two $R^4$s bound to the same carbon atom or to the same sulfur atom together represent one oxygen atom to form carbonyl or sulfoxide, or two $R^4$s bound to the same carbon atom together represent one sulfur atom to form thiocarbonyl, or four $R^4$s bound to the same sulfur atom together represent two oxygen atoms to form sulfone, or among the $R^4$s in the number of k, two $R^4$s bound to adjacent carbon atoms, respectively, together form benzo, pyrido, naphtho, cyclopropano, cyclobutano, cyclopentano, cyclopenteno, cyclohexano, cyclohexeno, cycloheptano or cyclohepteno, each of the above-mentioned groups from benzo to cyclohepteno being unsubstituted or substituted with 1 or more $R^5$s, wherein $R^5$(s) independently represent(s) fluorine, chlorine, bromine, iodine, nitro, $C_1$-$C_5$ alkyl, $C_7$-$C_{13}$ aralkyl, trifluoromethyl, trifluoromethoxy, cyano, $C_6$-$C_{12}$ aryl, isothiocyanato, $(CH_2)_p SR^6$, $(CH_2)_p S(O)R^6$, $(CH_2)_p S(O_2)R^6$, $(CH_2)_p OR^6$, $(CH_2)_p OC(=O)R^6$, $(CH_2)_p C(=O)R^6$, $(CH_2)_p CO_2 R^6$, $(CH_2)_p S(O_2)NR^7 R^8$, $(CH_2)_p C(=O)NR^7 R^8$, $(CH_2)_p NR^7 R^8$, $(CH_2)_p N(R^7)C(=O)R^8$, $(CH_2)_p N(R^7)S(O_2)R^8$;

p is an integer of 0 to 5;

$R^6$, $R^7$ and $R^8$ are independently hydrogen, $C_1$-$C_5$ alkyl, $C_3$-$C_7$ alkenyl, $C_6$-$C_{12}$ aryl or $C_7$-$C_{13}$ aralkyl;

$R^9$ is hydrogen, $C_1$-$C_5$ alkyl, $C_2$-$C_5$ alkenyl, $C_7$-$C_{13}$ aralkyl, $(CH_2)_p OR^6$ or $(CH_2)_p CO_2 R^6$ (wherein p and $R^6$ represent the same meanings as described above);

$R^{10}$ and $R^{11}$ are bound to form —O—, —S— or —CH$_2$—, or $R^{10}$ is hydrogen and $R^{11}$ is hydrogen, hydroxy, $C_1$-$C_5$ alkoxy or $C_1$-$C_5$ alkanoyloxy;

$R^{12}$ and $R^{13}$ together represent oxo, or $R^{12}$ is hydrogen and $R^{13}$ is hydrogen, hydroxy, $C_1$-$C_5$ alkoxy or $C_1$-$C_5$ alkanoyloxy; and the Formula (I) includes (+), (−) and (±) isomers]

or a pharmaceutically acceptable acid addition salt thereof.

The present invention also provides a use of a morphinan derivative having a nitrogen-containing cyclic substituent, represented by Formula (I) or a pharmaceutically acceptable acid addition salt thereof for the production of a therapeutic or prophylactic agent for functional bowel disorders.

The present invention further provides a method for therapy or prophylaxis of a functional bowel disorder, comprising administering an effective amount of a morphinan derivative having a nitrogen-containing cyclic substituent, represented by Formula (I) or a pharmaceutically acceptable acid addition salt thereof.

EFFECTS OF THE INVENTION

The therapeutic or prophylactic agent for functional bowel disorders according to the present invention has an excellent therapeutic or prophylactic effect against functional bowel disorders and the side effects thereof are small.

BEST MODE FOR CARRYING OUT THE INVENTION

As described above, the therapeutic or prophylactic agent for functional bowel disorders according to the present invention comprises as an effective ingredient the morphinan derivative having a nitrogen-containing cyclic substituent, represented by the above-described Formula (I) or a pharmaceutically acceptable acid addition salt thereof.

Among the compounds represented by Formula (I), those wherein Y is —C(=O)— are preferred, and those wherein both Y and Z are —C(=O)— are especially preferred.

$R^1$ is preferably hydrogen, $C_4$-$C_7$ cycloalkylalkyl, $C_6$-$C_8$ cycloalkenylalkyl, $C_6$-$C_{12}$ aryl or $C_3$-$C_7$ alkenyl, particularly, hydrogen, cyclopropylmethyl, 2-cyclopropylethyl, 3-cyclopropylpropyl, 4-cyclopropylbutyl, cyclobutylmethyl, cyclopentylmethyl, cyclohexylmethyl, cyclobutenylmethyl, 2-cyclobutenylethyl, 3-cyclobutenylpropyl, phenyl, naphthyl, allyl or prenyl. Among these, hydrogen, cyclopropylmethyl, cyclobutylmethyl, cyclopentylmethyl, cyclohexylmethyl, allyl and prenyl are preferred, and hydrogen, cyclopropylmethyl, cyclobutylmethyl and allyl are especially preferred.

$R^2$ and $R^3$ are preferably hydrogen, hydroxy, methoxy, ethoxy, allyloxy, benzyloxy, acetoxy or propionoxy, more preferably, hydrogen, hydroxy, methoxy or acetoxy.

—X— is preferably $C_2$-$C_4$ alkylene or alkenylene (one carbon atom therein may be replaced by a sulfur atom) constituting a part of the ring structure, more preferably, ethylene (—$CH_2$—$CH_2$—), vinylene (—CH=CH—), propenylene (—$CH_2$—CH=CH—) or —S—CH=CH—.

k is preferably an integer of 2 to 8, more preferably 2 to 6, still more preferably 2 or 6.

It is preferred that $R^4$ be $C_1$-$C_5$ alkyl, $C_1$-$C_5$ alkylidene, $C_7$-$C_{13}$ cycloalkylalkyl, $C_7$-$C_{13}$ aralkyl or $C_7$-$C_{13}$ aralkylidene, or that two $R^4$s bound to adjacent carbon atoms, respectively, together form benzo, pyrido, naphtho, cyclopropano, cyclobutano, cyclopentano, cyclopenteno, cyclohexano, cyclohexeno, cycloheptano or cyclohepteno, each of the above-mentioned groups from benzo to cyclohepteno being unsubstituted or substituted with 1 or more $R^5$s. In addition, the cases where X is —S—CH=CH—, and among the $R^4$s in the number of k, four $R^4$s bound to the same sulfur atom together represent two oxygen atoms to form sulfone are preferred. It is more preferred that $R^4$ be methyl, ethyl, ethylidene, propyl, propylidene, butyl, butylidene, benzyl, benzylidene, phenethyl, phenethylidene or cyclohexylmethyl, or that two $R^4$s bound to adjacent carbon atoms, respectively, together form benzo or cyclohexeno, which benzo or cyclohexeno is unsubstituted or substituted with 1 or more $R^5$s, more preferably that two $R^4$s bound to adjacent carbon atoms, respectively, together form benzo or cyclohexeno, which benzo or cyclohexeno is unsubstituted or substituted with 1 to 4 $R^5$s. In addition, the cases where X is —S—CH=CH—, and among the $R^4$s in the number of k, four $R^4$s bound to the same sulfur atom together represent two oxygen atoms to form sulfone are especially preferred. Although unsubstituted benzo or unsubstituted cyclohexeno is also preferred, the substituent(s) $R^5$(s) is(are) preferably and independently fluorine, chlorine, bromine, iodine, nitro, methyl, ethyl, propyl, benzyl, hydroxy, methoxy, ethoxy, trifluoromethyl, trifluoromethoxy, cyano, phenyl, isothiocyanato, mercapto, methylthio, methylsulfinyl, methylsulfonyl, hydroxymethyl, hydroxyethyl, methoxymethyl, ethoxymethyl, phenoxy, acetoxy, methoxycarbonyl, ethoxycarbonyl, methoxycarbonylmethyl, ethoxycarbonylmethyl, sulfamoyl, dimethylsulamoyl, dimethylcarbamoyl, dimethylamino, dimethylaminomethyl, dimethylaminoethyl, amino, acetamino, acetaminomethyl or methansulfonamide.

$R^9$ is preferably hydrogen, $C_1$-$C_5$ alkyl, allyl or benzyl, more preferably hydrogen or methyl.

It is preferred that $R^{10}$ and $R^{11}$ be bound to form —O—, or that $R^{10}$ be hydrogen and $R^{11}$ be hydrogen, hydroxy or methoxy, and more preferred that $R^{10}$ and $R^{11}$ be bound to form —O—.

It is preferred that $R^{12}$ and $R^{13}$ together form oxo, or that $R^{12}$ be hydrogen and $R^{13}$ be hydrogen or hydroxy. Especially preferably, both $R^{12}$ and $R^{13}$ are hydrogen, that is, unsubstituted one is especially preferred.

Especially preferred compounds represented by Formula (I) are those wherein Y is —C(=O)—; $R^1$ is hydrogen, $C_4$-$C_7$ cycloalkylalkyl, $C_5$-$C_8$ cycloalkenylalkyl, $C_6$-$C_{12}$ aryl or $C_3$-$C_7$ alkenyl;
Z is valence bond;
(1) X is propenylene (—$CH_2$—CH=CH—), k is 2, or
(2) X is —S—CH=CH—, k is 6, and four $R^4$s bound to the sulfur atom together represent two oxygen atoms to form sulfone; and
two $R^4$s bound to adjacent carbon atoms, respectively, together form benzo or cyclohexeno, which benzo or cyclohexeno is unsubstituted or substituted with 1 or more substituents $R^5$(s).

Compounds represented by Formula (I) which are also preferred are those wherein both Y and Z are —(C=O)—, $R^1$ is hydrogen, $C_4$-$C_7$ cycloalkylalkyl, $C_5$-$C_8$ cycloalkenylalkyl, $C_6$-$C_{12}$ aryl or $C_3$-$C_7$ alkenyl; k is an integer of 2 to 8; and two $R^4$s bound to adjacent carbon atoms, respectively, together form benzo, pyrido, naphtho, cyclopropano, cyclobutano, cyclopentano, cyclopenteno, cyclohexano, cyclohexeno, cycloheptano or cyclohepteno, each of the above-mentioned groups from benzo to cyclohepteno being unsubstituted or substituted with 1 or more $R^5$s.

Compounds represented by Formula (I) which are still also preferred are those wherein both Y and Z are —(C=O)—, $R^1$ is hydrogen, cyclopropylmethyl, cyclobutylmethyl or allyl; $R^2$ and $R^3$ are hydrogen, hydroxy, methoxy or acetoxy; —X— is vinylene; k is 2; two $R^4$s together form benzo or cyclohexeno, which benzo or cyclohexeno is unsubstituted or substituted with 1 to 4 substituents $R^5$(s); $R^5$(s) is(are) independently fluorine, chlorine, bromine, iodine, nitro, methyl, ethyl, propyl, benzyl, hydroxyl, methoxy, ethoxy, trifluoromethyl, trifluoromethoxy, cyano, phenyl, isothiocyanato, mercapto, methylthio, methylsulfinyl, methylsulfonyl, hydroxymethyl, hydroxyethyl, methoxymethyl, ethoxymethyl, methoxyethyl, phenoxy, acetoxy, methoxycarbonyl, ethoxycarbonyl, methoxycarbonylmethyl, ethoxycarbonylmethyl, sulfamoyl, dimethylsulamoyl, dimethylcarbamoyl, dimethylamino, dimethylaminomethyl, dimethylaminoethyl, amino, acetamino, acetaminomethyl or methansulfonamide; $R^9$ is hydrogen or methyl; $R^{10}$ and $R^{11}$ are bound to form —O—; and both $R^{12}$ and $R^{13}$ are hydrogen.

Preferred examples of the pharmaceutically acceptable acid addition salts include inorganic acid salts such as hydrochloric acid salt, sulfuric acid salt, nitric acid salt, hydrobromic acid salt, hydroiodic acid salt and phosphoric acid salt; organic carboxylic acid salts such as acetic acid salt, lactic acid salt, citric acid salt, oxalic acid salt, glutaric acid salt, malic acid salt, tartaric acid salt, fumaric acid salt, mandelic acid salt, maleic acid salt, benzoic acid salt and phthalic acid salt; and organic sulfonic acid salts such as methanesulfonic acid salt, ethanesulfonic acid salt, benzenesulfonic acid salt, p-toluenesulfonic acid salt and camphorsulfonic acid salt. Among these, hydrochloric acid salt, hydrobromic acid salt, phosphoric acid salt, tartaric acid salt, methanesulfonic acid salt and the like are preferred, but the acid addition salt is not restricted thereto.

Among the compounds of the Formula (I) according to the present invention, specific examples of those wherein —X— is vinylene (—CH=CH—); Y and Z are —C(=O)—; two $R^4$s bound to adjacent carbon atoms together form benzo or cyclohexeno, which benzo or cyclohexeno is unsubstituted or substituted with one or more substituents $R^5$(s); $R^9$, $R^{12}$ and $R^{13}$ are hydrogen; $R^{10}$ and $R^{11}$ are bound to form —O—, that is, those represented by the Formula (Ia) or (Ia') below, as well as those wherein —X— is —S—CH=CH—: Y is —C(=O)—; Z is valence bond; four $R^4$s bound to the sulfur atom together represent two oxygen atoms to form sulfone; two $R^4$s bound to adjacent carbon atoms together form benzo which is unsubstituted or substituted with one or more substituents $R^5$(s); $R^9$, $R^{12}$ and $R^{13}$ are hydrogen; and $R^{10}$ and $R^{11}$ are bound to form —O—, that is, those represented by the Formula (Ia") are shown in Table 1. In the tables described below, CPM means cyclopropylmethyl; the number attached to the substituent $R^5$ is the position of the substituent on the benzene ring in the phthalimide structure, on the cyclohexene ring in the tetrahydrophthalimide structure, or on the benzene ring in the O-sulfone benzoic imide structure, shown in the formulae below; and the bond at 6-position is α or β.

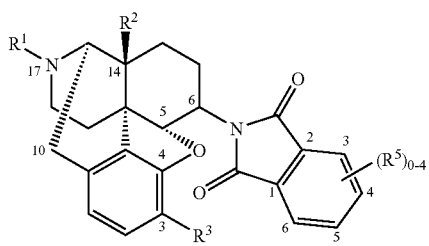

(Ia)

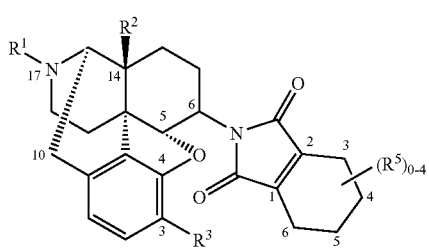

(Ia')

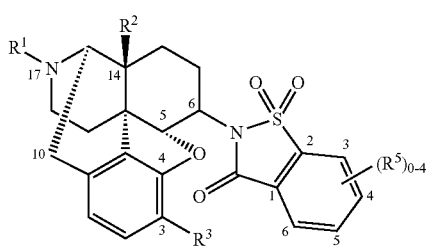

(Ia'')

Among the compounds represented by Formula (Ia), the compound wherein $R^1$ is cyclopropylmethyl, $R^2$ and $R^3$ are hydroxy, $R^5$ is 4-fluoro, and the configuration of the bond at the 6-position is β, that is, the compound of the following formula:

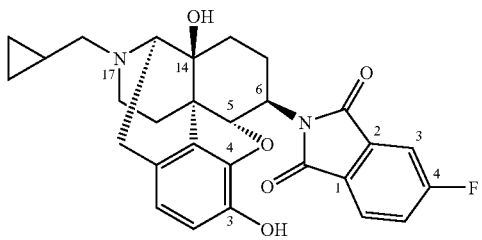

is named N-[17-(cyclopropylmethyl)-4,5α-epoxy-3,14-dihydroxymorphinan-6β-yl]-4-fluorophthalimide.

TABLE 1

| $R^1$ | $R^2$ | $R^3$ | $R^5$ |
|---|---|---|---|
| CPM | OH | OH | (unsubstituted) |
| CPM | OH | OH | 3-F |
| CPM | OH | OH | 4-F |
| CPM | OH | OH | 3,6-F |
| CPM | OH | OH | 4,5-F |
| CPM | OH | OH | 3,4,5,6-F |
| CPM | OH | OH | 3-Cl |
| CPM | OH | OH | 4-Cl |
| CPM | OH | OH | 3,6-Cl |
| CPM | OH | OH | 4,5-Cl |
| CPM | OH | OH | 3-Br |
| CPM | OH | OH | 4-Br |
| CPM | OH | OH | 3,6-Br |

TABLE 1-continued

| $R^1$ | $R^2$ | $R^3$ | $R^5$ |
|---|---|---|---|
| CPM | OH | OH | 4,5-Br |
| CPM | OH | OH | 3-Me |
| CPM | OH | OH | 4-Me |
| CPM | OH | OH | 3,6-Me |
| CPM | OH | OH | 4,5-Me |
| CPM | OH | OH | 3-OMe |
| CPM | OH | OH | 4-OMe |
| CPM | OH | OH | 3,6-OMe |
| CPM | OH | OH | 4,5-OMe |
| CPM | OH | OH | 3-OH |
| CPM | OH | OH | 4-OH |
| CPM | OH | OH | 3,6-OH |
| CPM | OH | OH | 4,5-OH |
| CPM | OH | OH | 3-NO$_2$ |
| CPM | OH | OH | 4-NO$_2$ |
| CPM | OH | OH | 3,6-NO$_2$ |
| CPM | OH | OH | 4,5-NO$_2$ |
| CPM | OH | OH | 3-NH$_2$ |
| CPM | OH | OH | 4-NH$_2$ |
| CPM | OH | OH | 3,6-NH$_2$ |
| CPM | OH | OH | 4,5-NH$_2$ |
| allyl | OH | OH | (unsubstituted) |
| allyl | OH | OH | 3-F |
| allyl | OH | OH | 4-F |
| allyl | OH | OH | 3,6-F |
| allyl | OH | OH | 4,5-F |
| allyl | OH | OH | 3,4,5,6-F |
| allyl | OH | OH | 3-Cl |
| allyl | OH | OH | 4-Cl |
| allyl | OH | OH | 3,6-Cl |
| allyl | OH | OH | 4,5-Cl |
| allyl | OH | OH | 3-Br |
| allyl | OH | OH | 4-Br |
| allyl | OH | OH | 3,6-Br |
| allyl | OH | OH | 4,5-Br |
| allyl | OH | OH | 3-Me |
| allyl | OH | OH | 4-Me |
| allyl | OH | OH | 3,6-Me |
| allyl | OH | OH | 4,5-Me |
| allyl | OH | OH | 3-OMe |
| allyl | OH | OH | 4-OMe |
| allyl | OH | OH | 3,6-OMe |
| allyl | OH | OH | 4,5-OMe |
| allyl | OH | OH | 3-OH |
| allyl | OH | OH | 4-OH |
| allyl | OH | OH | 3,6-OH |
| allyl | OH | OH | 4,5-OH |
| allyl | OH | OH | 3-NO$_2$ |
| allyl | OH | OH | 4-NO$_2$ |
| allyl | OH | OH | 3,6-NO$_2$ |
| allyl | OH | OH | 4,5-NO$_2$ |
| allyl | OH | OH | 3-NH$_2$ |
| allyl | OH | OH | 4-NH$_2$ |
| allyl | OH | OH | 3,6-NH$_2$ |
| allyl | OH | OH | 4,5-NH$_2$ |
| CPM | H | OH | (unsubstituted) |
| CPM | H | OH | 3-F |
| CPM | H | OH | 4-F |
| CPM | H | OH | 3,6-F |
| CPM | H | OH | 4,5-F |
| CPM | H | OH | 3,4,5,6-F |
| CPM | H | OH | 3-Cl |
| CPM | H | OH | 4-Cl |
| CPM | H | OH | 3,6-Cl |
| CPM | H | OH | 4,5-Cl |
| CPM | H | OH | 3-Br |
| CPM | H | OH | 4-Br |
| CPM | H | OH | 3,6-Br |
| CPM | H | OH | 4,5-Br |
| CPM | H | OH | 3-Me |
| CPM | H | OH | 4-Me |
| CPM | H | OH | 3,6-Me |
| CPM | H | OH | 4,5-Me |
| CPM | H | OH | 3-OMe |
| CPM | H | OH | 4-OMe |
| CPM | H | OH | 3,6-OMe |
| CPM | H | OH | 4,5-OMe |
| CPM | H | OH | 3-OH |

TABLE 1-continued

| R¹ | R² | R³ | R⁵ |
|---|---|---|---|
| CPM | H | OH | 4-OH |
| CPM | H | OH | 3,6-OH |
| CPM | H | OH | 4,5-OH |
| CPM | H | OH | 3-NO₂ |
| CPM | H | OH | 4-NO₂ |
| CPM | H | OH | 3,6-NO₂ |
| CPM | H | OH | 4,5-NO₂ |
| CPM | H | OH | 3-NH₂ |
| CPM | H | OH | 4-NH₂ |
| CPM | H | OH | 3,6-NH₂ |
| CPM | H | OH | 4,5-NH₂ |
| allyl | H | OH | (unsubstituted) |
| allyl | H | OH | 3-F |
| allyl | H | OH | 4-F |
| allyl | H | OH | 3,6-F |
| allyl | H | OH | 4,5-F |
| allyl | H | OH | 3,4,5,6-F |
| allyl | H | OH | 3-Cl |
| allyl | H | OH | 4-Cl |
| allyl | H | OH | 3,6-Cl |
| allyl | H | OH | 4,5-Cl |
| allyl | H | OH | 3-Br |
| allyl | H | OH | 4-Br |
| allyl | H | OH | 3,6-Br |
| allyl | H | OH | 4,5-Br |
| allyl | H | OH | 3-Me |
| allyl | H | OH | 4-Me |
| allyl | H | OH | 3,6-Me |
| allyl | H | OH | 4,5-Me |
| allyl | H | OH | 3-OMe |
| allyl | H | OH | 4-OMe |
| allyl | H | OH | 3,6-OMe |
| allyl | H | OH | 4,5-OMe |
| allyl | H | OH | 3-OH |
| allyl | H | OH | 4-OH |
| allyl | H | OH | 3,6-OH |
| allyl | H | OH | 4,5-OH |
| allyl | H | OH | 3-NO₂ |
| allyl | H | OH | 4-NO₂ |
| allyl | H | OH | 3,6-NO₂ |
| allyl | H | OH | 4,5-NO₂ |
| allyl | H | OH | 3-NH₂ |
| allyl | H | OH | 4-NH₂ |
| allyl | H | OH | 3,6-NH₂ |
| allyl | H | OH | 4,5-NH₂ |
| CPM | OAc | OH | (unsubstituted) |
| CPM | OAc | OH | 3-F |
| CPM | OAc | OH | 4-F |
| CPM | OAc | OH | 3,6-F |
| CPM | OAc | OH | 4,5-F |
| CPM | OAc | OH | 3,4,5,6-F |
| CPM | OAc | OH | 3-Cl |
| CPM | OAc | OH | 4-Cl |
| CPM | OAc | OH | 3,6-Cl |
| CPM | OAc | OH | 4,5-Cl |
| CPM | OAc | OH | 3-Br |
| CPM | OAc | OH | 4-Br |
| CPM | OAc | OH | 3,6-Br |
| CPM | OAc | OH | 4,5-Br |
| CPM | OAc | OH | 3-Me |
| CPM | OAc | OH | 4-Me |
| CPM | OAc | OH | 3,6-Me |
| CPM | OAc | OH | 4,5-Me |
| CPM | OAc | OH | 3-OMe |
| CPM | OAc | OH | 4-OMe |
| CPM | OAc | OH | 3,6-OMe |
| CPM | OAc | OH | 4,5-OMe |
| CPM | OAc | OH | 3-OH |
| CPM | OAc | OH | 4-OH |
| CPM | OAc | OH | 3,6-OH |
| CPM | OAc | OH | 4,5-OH |
| CPM | OAc | OH | 3-NO₂ |
| CPM | OAc | OH | 4-NO₂ |
| CPM | OAc | OH | 3,6-NO₂ |
| CPM | OAc | OH | 4,5-NO₂ |
| CPM | OAc | OH | 3-NH₂ |
| CPM | OAc | OH | 4-NH₂ |
| CPM | OAc | OH | 3,6-NH₂ |
| CPM | OAc | OH | 4,5-NH₂ |
| allyl | OAc | OH | (unsubstituted) |
| allyl | OAc | OH | 3-F |
| allyl | OAc | OH | 4-F |
| allyl | OAc | OH | 3,6-F |
| allyl | OAc | OH | 4,5-F |
| allyl | OAc | OH | 3,4,5,6-F |
| allyl | OAc | OH | 3-Cl |
| allyl | OAc | OH | 4-Cl |
| allyl | OAc | OH | 3,6-Cl |
| allyl | OAc | OH | 4,5-Cl |
| allyl | OAc | OH | 3-Br |
| allyl | OAc | OH | 4-Br |
| allyl | OAc | OH | 3,6-Br |
| allyl | OAc | OH | 4,5-Br |
| allyl | OAc | OH | 3-Me |
| allyl | OAc | OH | 4-Me |
| allyl | OAc | OH | 3,6-Me |
| allyl | OAc | OH | 4,5-Me |
| allyl | OAc | OH | 3-OMe |
| allyl | OAc | OH | 4-OMe |
| allyl | OAc | OH | 3,6-OMe |
| allyl | OAc | OH | 4,5-OMe |
| allyl | OAc | OH | 3-OH |
| allyl | OAc | OH | 4-OH |
| allyl | OAc | OH | 3,6-OH |
| allyl | OAc | OH | 4,5-OH |
| allyl | OAc | OH | 3-NO₂ |
| allyl | OAc | OH | 4-NO₂ |
| allyl | OAc | OH | 3,6-NO₂ |
| allyl | OAc | OH | 4,5-NO₂ |
| allyl | OAc | OH | 3-NH₂ |
| allyl | OAc | OH | 4-NH₂ |
| allyl | OAc | OH | 3,6-NH₂ |
| allyl | OAc | OH | 4,5-NH₂ |

Among the compounds of the Formula (I) according to the present invention, specific examples of those wherein —X— is propenylene (—CH$_2$—CH═CH—); Y is —C(═O)—; Z is valence bond; two R⁴'s bound to adjacent carbon atoms together form benzo which is unsubstituted or substituted with one or more substituents R⁵(s); R⁹, R¹² and R¹³ are hydrogen; R¹⁰ and R¹¹ are bound to form —O—, that is, those represented by the Formula (Ib) below are shown in Table 1. In Table 2, a hyphen means that the substituent is not shown in the chemical formula (i.e., it is a hydrogen atom) (the hyphens in other tables have the same meaning); the number attached to the substituent R⁵ is the position of the substituent on the dihydroisoindole ring, shown in the formula below; and the bond at 6-position is α or β.

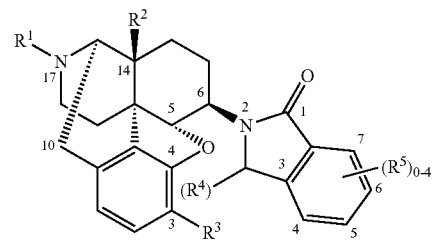

(Ib)

Among the compounds represented by Formula (Ib), the compound wherein R¹ is cyclopropylmethyl, R² and R³ are hydroxy, R⁵ is 6-fluoro, and the configuration of the bond at the 6-position is β, that is, the compound of the following formula:

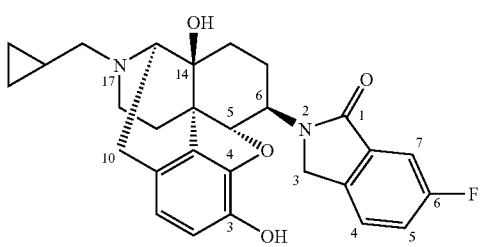

is named 2-[17-(cyclopropylmethyl)-4,5α-epoxy-3,14-dihydroxymorphinan-6β-yl]-6-fluoro-2,3-dihydro-isoindol-1-one.

TABLE 2

| $R^1$ | $R^2$ | $R^3$ | $R^4$ | $R^5$ |
|---|---|---|---|---|
| CPM | OH | OH | — | (unsubstituted) |
| CPM | OH | OH | — | 4-F |
| CPM | OH | OH | — | 5-F |
| CPM | OH | OH | — | 6-F |
| CPM | OH | OH | — | 7-F |
| CPM | OH | OH | — | 5,6-F |
| CPM | OH | OH | — | 4,5,6,7-F |
| CPM | OH | OH | — | 4-Cl |
| CPM | OH | OH | — | 5-Cl |
| CPM | OH | OH | — | 6-Cl |
| CPM | OH | OH | — | 7-Cl |
| CPM | OH | OH | — | 5,6-Cl |
| CPM | OH | OH | — | 4-Me |
| CPM | OH | OH | — | 5-Me |
| CPM | OH | OH | — | 6-Me |
| CPM | OH | OH | — | 7-Me |
| CPM | OH | OH | — | 5,6-Me |
| CPM | OH | OH | — | 4-OMe |
| CPM | OH | OH | — | 5-OMe |
| CPM | OH | OH | — | 6-OMe |
| CPM | OH | OH | — | 7-OMe |
| CPM | OH | OH | — | 5,6-OMe |
| allyl | OH | OH | — | (unsubstituted) |
| allyl | OH | OH | — | 4-F |
| allyl | OH | OH | — | 5-F |
| allyl | OH | OH | — | 6-F |
| allyl | OH | OH | — | 7-F |
| allyl | OH | OH | — | 5,6-F |
| allyl | OH | OH | — | 4,5,6,7-F |
| allyl | OH | OH | — | 4-Cl |
| allyl | OH | OH | — | 5-Cl |
| allyl | OH | OH | — | 6-Cl |
| allyl | OH | OH | — | 7-Cl |
| allyl | OH | OH | — | 5,6-Cl |
| allyl | OH | OH | — | 4-Me |
| allyl | OH | OH | — | 5-Me |
| allyl | OH | OH | — | 6-Me |
| allyl | OH | OH | — | 7-Me |
| allyl | OH | OH | — | 5,6-Me |
| allyl | OH | OH | — | 4-OMe |
| allyl | OH | OH | — | 5-OMe |
| allyl | OH | OH | — | 6-OMe |
| allyl | OH | OH | — | 7-OMe |
| allyl | OH | OH | — | 5,6-OMe |
| CPM | H | OH | — | (unsubstituted) |
| CPM | H | OH | — | 4-F |
| CPM | H | OH | — | 5-F |
| CPM | H | OH | — | 6-F |
| CPM | H | OH | — | 7-F |
| CPM | H | OH | — | 5,6-F |
| CPM | H | OH | — | 4,5,6,7-F |
| CPM | H | OH | — | 4-Cl |
| CPM | H | OH | — | 5-Cl |
| CPM | H | OH | — | 6-Cl |
| CPM | H | OH | — | 7-Cl |
| CPM | H | OH | — | 5,6-Cl |
| CPM | H | OH | — | 4-Me |
| CPM | H | OH | — | 5-Me |
| CPM | H | OH | — | 6-Me |
| CPM | H | OH | — | 7-Me |
| CPM | H | OH | — | 5,6-Me |
| CPM | H | OH | — | 4-OMe |
| CPM | H | OH | — | 5-OMe |
| CPM | H | OH | — | 6-OMe |
| CPM | H | OH | — | 7-OMe |
| CPM | H | OH | — | 5,6-OMe |
| allyl | H | OH | — | (unsubstituted) |
| allyl | H | OH | — | 4-F |
| allyl | H | OH | — | 5-F |
| allyl | H | OH | — | 6-F |
| allyl | H | OH | — | 7-F |
| allyl | H | OH | — | 5,6-F |
| allyl | H | OH | — | 4,5,6,7-F |
| allyl | H | OH | — | 4-Cl |
| allyl | H | OH | — | 5-Cl |
| allyl | H | OH | — | 6-Cl |
| allyl | H | OH | — | 7-Cl |
| allyl | H | OH | — | 5,6-Cl |
| allyl | H | OH | — | 4-Me |
| allyl | H | OH | — | 5-Me |
| allyl | H | OH | — | 6-Me |
| allyl | H | OH | — | 7-Me |
| allyl | H | OH | — | 5,6-Me |
| allyl | H | OH | — | 4-OMe |
| allyl | H | OH | — | 5-OMe |
| allyl | H | OH | — | 6-OMe |
| allyl | H | OH | — | 7-OMe |
| allyl | H | OH | — | 5,6-OMe |
| CPM | OH | OH | OH | (unsubstituted) |
| CPM | OH | OH | OH | 4-F |
| CPM | OH | OH | OH | 5-F |
| CPM | OH | OH | OH | 6-F |
| CPM | OH | OH | OH | 7-F |
| CPM | OH | OH | OH | 5,6-F |
| CPM | OH | OH | OH | 4,5,6,7-F |
| CPM | OH | OH | OH | 4-Cl |
| CPM | OH | OH | OH | 5-Cl |
| CPM | OH | OH | OH | 6-Cl |
| CPM | OH | OH | OH | 7-Cl |
| CPM | OH | OH | OH | 5,6-Cl |
| CPM | OH | OH | OH | 4-Me |
| CPM | OH | OH | OH | 5-Me |
| CPM | OH | OH | OH | 6-Me |
| CPM | OH | OH | OH | 7-Me |
| CPM | OH | OH | OH | 5,6-Me |
| CPM | OH | OH | OH | 4-OMe |
| CPM | OH | OH | OH | 5-OMe |
| CPM | OH | OH | OH | 6-OMe |
| CPM | OH | OH | OH | 7-OMe |
| CPM | OH | OH | OH | 5,6-OMe |
| allyl | OH | OH | OH | (unsubstituted) |
| allyl | OH | OH | OH | 4-F |
| allyl | OH | OH | OH | 5-F |
| allyl | OH | OH | OH | 6-F |
| allyl | OH | OH | OH | 7-F |
| allyl | OH | OH | OH | 5,6-F |
| allyl | OH | OH | OH | 4,5,6,7-F |
| allyl | OH | OH | OH | 4-Cl |
| allyl | OH | OH | OH | 5-Cl |
| allyl | OH | OH | OH | 6-Cl |
| allyl | OH | OH | OH | 7-Cl |
| allyl | OH | OH | OH | 5,6-Cl |
| allyl | OH | OH | OH | 4-Me |
| allyl | OH | OH | OH | 5-Me |
| allyl | OH | OH | OH | 6-Me |
| allyl | OH | OH | OH | 7-Me |
| allyl | OH | OH | OH | 5,6-Me |
| allyl | OH | OH | OH | 4-OMe |
| allyl | OH | OH | OH | 5-OMe |
| allyl | OH | OH | OH | 6-OMe |
| allyl | OH | OH | OH | 7-OMe |
| allyl | OH | OH | OH | 5,6-OMe |
| CPM | H | OH | OH | (unsubstituted) |
| CPM | H | OH | OH | 4-F |
| CPM | H | OH | OH | 5-F |
| CPM | H | OH | OH | 6-F |
| CPM | H | OH | OH | 7-F |

TABLE 2-continued

| R¹ | R² | R³ | R⁴ | R⁵ |
|---|---|---|---|---|
| CPM | H | OH | OH | 5,6-F |
| CPM | H | OH | OH | 4,5,6,7-F |
| CPM | H | OH | OH | 4-Cl |
| CPM | H | OH | OH | 5-Cl |
| CPM | H | OH | OH | 6-Cl |
| CPM | H | OH | OH | 7-Cl |
| CPM | H | OH | OH | 5,6-Cl |
| CPM | H | OH | OH | 4-Me |
| CPM | H | OH | OH | 5-Me |
| CPM | H | OH | OH | 6-Me |
| CPM | H | OH | OH | 7-Me |
| CPM | H | OH | OH | 5,6-Me |
| CPM | H | OH | OH | 4-OMe |
| CPM | H | OH | OH | 5-OMe |
| CPM | H | OH | OH | 6-OMe |
| CPM | H | OH | OH | 7-OMe |
| CPM | H | OH | OH | 5,6-OMe |
| allyl | H | OH | OH | (unsubstituted) |
| allyl | H | OH | OH | 4-F |
| allyl | H | OH | OH | 5-F |
| allyl | H | OH | OH | 6-F |
| allyl | H | OH | OH | 7-F |
| allyl | H | OH | OH | 5,6-F |
| allyl | H | OH | OH | 4,5,6,7-F |
| allyl | H | OH | OH | 4-Cl |
| allyl | H | OH | OH | 5-Cl |
| allyl | H | OH | OH | 6-Cl |
| allyl | H | OH | OH | 7-Cl |
| allyl | H | OH | OH | 5,6-Cl |
| allyl | H | OH | OH | 4-Me |
| allyl | H | OH | OH | 5-Me |
| allyl | H | OH | OH | 6-Me |
| allyl | H | OH | OH | 7-Me |
| allyl | H | OH | OH | 5,6-Me |
| allyl | H | OH | OH | 4-OMe |
| allyl | H | OH | OH | 5-OMe |
| allyl | H | OH | OH | 6-OMe |
| allyl | H | OH | OH | 7-OMe |
| allyl | H | OH | OH | 5,6-OMe |
| CPM | OH | OH | CH₂COOMe | (unsubstituted) |
| CPM | OH | OH | CH₂COOMe | 4-F |
| CPM | OH | OH | CH₂COOMe | 5-F |
| CPM | OH | OH | CH₂COOMe | 6-F |
| CPM | OH | OH | CH₂COOMe | 7-F |
| CPM | OH | OH | CH₂COOMe | 5,6-F |
| CPM | OH | OH | CH₂COOMe | 4,5,6,7-F |
| CPM | OH | OH | CH₂COOMe | 4-Cl |
| CPM | OH | OH | CH₂COOMe | 5-Cl |
| CPM | OH | OH | CH₂COOMe | 6-Cl |
| CPM | OH | OH | CH₂COOMe | 7-Cl |
| CPM | OH | OH | CH₂COOMe | 5,6-Cl |
| CPM | OH | OH | CH₂COOMe | 4-Me |
| CPM | OH | OH | CH₂COOMe | 5-Me |
| CPM | OH | OH | CH₂COOMe | 6-Me |
| CPM | OH | OH | CH₂COOMe | 7-Me |
| CPM | OH | OH | CH₂COOMe | 5,6-Me |
| CPM | OH | OH | CH₂COOMe | 4-OMe |
| CPM | OH | OH | CH₂COOMe | 5-OMe |
| CPM | OH | OH | CH₂COOMe | 6-OMe |
| CPM | OH | OH | CH₂COOMe | 7-OMe |
| CPM | OH | OH | CH₂COOMe | 5,6-OMe |
| allyl | OH | OH | CH₂COOMe | (unsubstituted) |
| allyl | OH | OH | CH₂COOMe | 4-F |
| allyl | OH | OH | CH₂COOMe | 5-F |
| allyl | OH | OH | CH₂COOMe | 6-F |
| allyl | OH | OH | CH₂COOMe | 7-F |
| allyl | OH | OH | CH₂COOMe | 5,6-F |
| allyl | OH | OH | CH₂COOMe | 4,5,6,7-F |
| allyl | OH | OH | CH₂COOMe | 4-Cl |
| allyl | OH | OH | CH₂COOMe | 5-Cl |
| allyl | OH | OH | CH₂COOMe | 6-Cl |
| allyl | OH | OH | CH₂COOMe | 7-Cl |
| allyl | OH | OH | CH₂COOMe | 5,6-Cl |
| allyl | OH | OH | CH₂COOMe | 4-Me |
| allyl | OH | OH | CH₂COOMe | 5-Me |
| allyl | OH | OH | CH₂COOMe | 6-Me |
| allyl | OH | OH | CH₂COOMe | 7-Me |
| allyl | OH | OH | CH₂COOMe | 5,6-Me |
| allyl | OH | OH | CH₂COOMe | 4-OMe |
| allyl | OH | OH | CH₂COOMe | 5-OMe |
| allyl | OH | OH | CH₂COOMe | 6-OMe |
| allyl | OH | OH | CH₂COOMe | 7-OMe |
| allyl | OH | OH | CH₂COOMe | 5,6-OMe |
| CPM | H | OH | CH₂COOMe | (unsubstituted) |
| CPM | H | OH | CH₂COOMe | 4-F |
| CPM | H | OH | CH₂COOMe | 5-F |
| CPM | H | OH | CH₂COOMe | 6-F |
| CPM | H | OH | CH₂COOMe | 7-F |
| CPM | H | OH | CH₂COOMe | 5,6-F |
| CPM | H | OH | CH₂COOMe | 4,5,6,7-F |
| CPM | H | OH | CH₂COOMe | 4-Cl |
| CPM | H | OH | CH₂COOMe | 5-Cl |
| CPM | H | OH | CH₂COOMe | 6-Cl |
| CPM | H | OH | CH₂COOMe | 7-Cl |
| CPM | H | OH | CH₂COOMe | 5,6-Cl |
| CPM | H | OH | CH₂COOMe | 4-Me |
| CPM | H | OH | CH₂COOMe | 5-Me |
| CPM | H | OH | CH₂COOMe | 6-Me |
| CPM | H | OH | CH₂COOMe | 7-Me |
| CPM | H | OH | CH₂COOMe | 5,6-Me |
| CPM | H | OH | CH₂COOMe | 4-OMe |
| CPM | H | OH | CH₂COOMe | 5-OMe |
| CPM | H | OH | CH₂COOMe | 6-OMe |
| CPM | H | OH | CH₂COOMe | 7-OMe |
| CPM | H | OH | CH₂COOMe | 5,6-OMe |
| allyl | H | OH | CH₂COOMe | (unsubstituted) |
| allyl | H | OH | CH₂COOMe | 4-F |
| allyl | H | OH | CH₂COOMe | 5-F |
| allyl | H | OH | CH₂COOMe | 6-F |
| allyl | H | OH | CH₂COOMe | 7-F |
| allyl | H | OH | CH₂COOMe | 5,6-F |
| allyl | H | OH | CH₂COOMe | 4,5,6,7-F |
| allyl | H | OH | CH₂COOMe | 4-Cl |
| allyl | H | OH | CH₂COOMe | 5-Cl |
| allyl | H | OH | CH₂COOMe | 6-Cl |
| allyl | H | OH | CH₂COOMe | 7-Cl |
| allyl | H | OH | CH₂COOMe | 5,6-Cl |
| allyl | H | OH | CH₂COOMe | 4-Me |
| allyl | H | OH | CH₂COOMe | 5-Me |
| allyl | H | OH | CH₂COOMe | 6-Me |
| allyl | H | OH | CH₂COOMe | 7-Me |
| allyl | H | OH | CH₂COOMe | 5,6-Me |
| allyl | H | OH | CH₂COOMe | 4-OMe |
| allyl | H | OH | CH₂COOMe | 5-OMe |
| allyl | H | OH | CH₂COOMe | 6-OMe |
| allyl | H | OH | CH₂COOMe | 7-OMe |
| allyl | H | OH | CH₂COOMe | 5,6-OMe |

Among the morphinan derivatives having the nitrogen-containing cyclic substituent, represented by Formula (I), or the pharmaceutically acceptable acid addition salts thereof, which are used as an effective ingredient of the therapeutic or prophylactic agent for functional bowel disorders according to the present invention, those wherein both $R^{12}$ and $R^{13}$ are hydrogen, that is, the compounds represented by Formula (Ic) (wherein $R^1$, $R^2$, $R^3$, $R^4$, $R^9$, $R^{10}$, $R^{11}$, k, X, Y and Z have the same meanings as described above) or the pharmaceutically acceptable acid addition salts thereof may be, concretely, produced by the method described in International Publication No. WO 04/033457.

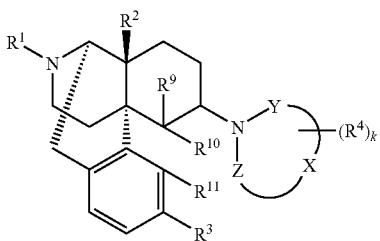

Among the morphinan derivatives having the nitrogen-containing cyclic substituent, represented by Formula (I), or method described in International Publication No. WO 04/033457 to the intermediate represented by Formula (IIb) (wherein $R^1$, $R^2$, $R^3$, $R^9$, $R^{10}$, $R^{11}$, $R^{12'}$ and $R^{13'}$ have the same meanings as described above, ••• is oxo or dibenzylamino) obtained by oxidizing the benzyl position of the morphinan derivative represented by Formula (IIa) (wherein $R^1$, $R^2$, $R^3$, $R^9$, $R^{10}$ and $R^{11}$ have the same meanings as described above, ••• Q is oxo or dibenzylamino). Oxidation of the benzyl position may be attained by directly introducing a hydroxy group or an oxo group, by introducing an oxo group and then reducing it to a hydroxy group, or by introducing a hydroxyl group and then oxidizing it to an oxo group. Depending on the type of the substituent, protection and deprotection steps may be added as required.

Scheme 1

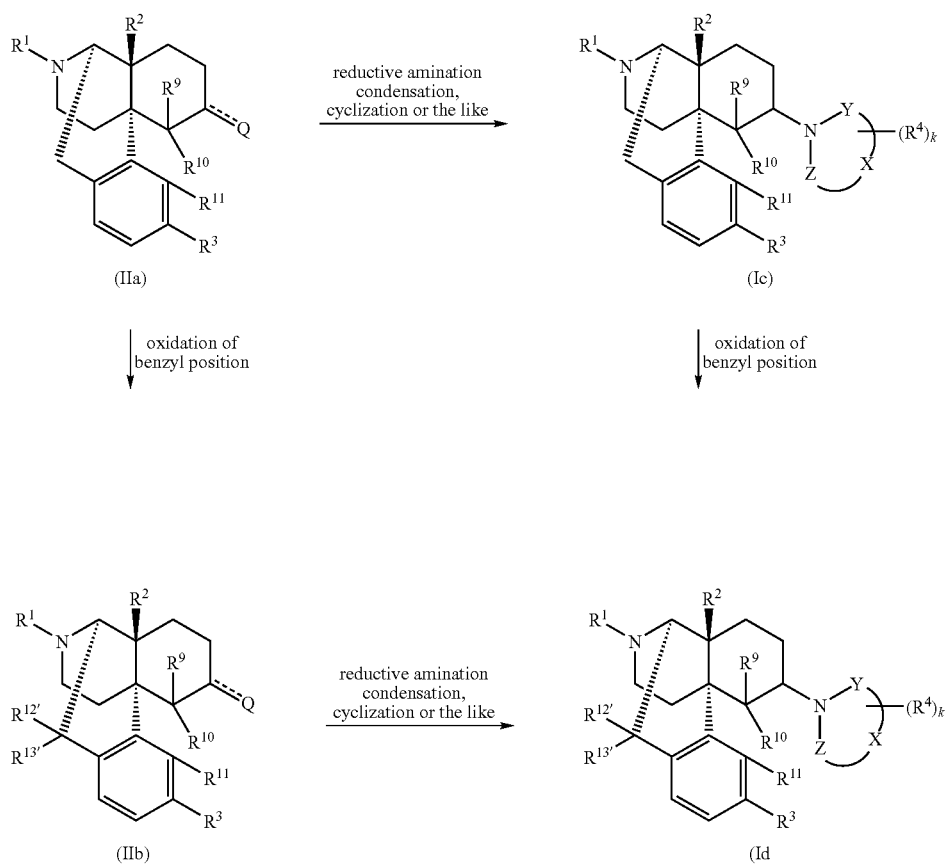

the pharmaceutically acceptable acid addition salts thereof, which are used as an effective ingredient of the therapeutic or prophylactic agent for functional bowel disorders according to the present invention, those wherein both $R^{12}$ and $R^{13}$ are $R^{12'}$ and $R^{13'}$ (wherein $R^{12'}$ and $R^{13'}$ together represent oxo, or $R^{12'}$ is hydrogen and $R^{13'}$ is hydroxy, $C_1$-$C_5$ alkoxy or $C_1$-$C_5$ alkanoyloxy), that is, the compounds represented by Formula (Id) (wherein $R^1$, $R^2$, $R^3$, $R^4$, $R^9$, $R^{10}$, $R^{11}$, k, X, Y and Z have the same meanings as described above) may be produced, as shown in Scheme 1, by directly oxidizing the benzyl position of the morphinan derivative having the nitrogen-containing cyclic substituent, represented by Formula (Ic) (wherein $R^1$, $R^2$, $R^3$, $R^4$, $R^9$, $R^{10}$, $R^{11}$, k, X, Y and Z have the same meanings as described above) obtained by the method described in International Publication WO 04/033457, or by applying the In the oxidation step, any oxidizing agent which may usually be used for the oxidation of the benzyl position may be employed. For introducing a hydroxy group, for example, manganese (III) salts such as manganese (III) acetate; lead compounds such as lead tetraacetate; organic peroxides such as t-butylhydro peroxide and benzoyl peroxide; cerium compounds such as ceric(IV) ammonium nitrate (CAN); and oxygen may be used as the oxidizing agent. Among these oxidizing agents, ceric(IV) ammonium nitrate is useful because α-hydroxy compound may be selectively obtained in some cases. By using an oxidizing agent containing an organic acid such as acetic acid, an alkanoyloxy group such as acetoxy group may be effectively introduced in some cases.

In case of introducing an oxo group, for example, permanganates such as potassium permanganate; manganese compounds such as manganese dioxide; chromium compounds such as chromium oxide and sodium chromate; selenium compounds such as selenium dioxide; periodates such as sodium periodate; quinones such as DDQ; silver compounds such as silver oxide; cerium compounds such as ceric(IV) ammonium nitrate (CAN); halogens (chlorine, bromine and iodine); oxygen; and hydrogen peroxide may be employed.

The reaction conditions such as reaction solvent, reaction temperature, reaction time, concentration of the substrate, equivalent ratio of the reactants and the like may be appropriately selected depending on the oxidizing agent employed. For example, in cases where a cerium compound such as ceric(IV) ammonium nitrate (CAN) is used, the desired compound may be obtained with a high yield by reacting 4 equivalents of the oxidizing agent with respect to the substrate at room temperature in acetonitrile/water mixed solvent system.

In cases where an oxo group is reduced to a hydroxy group, any reducing agent which is usually employed in the reduction of carbonyl compounds may be employed, and a hydride reducing agent such as sodium borohydride or lithium aluminium hydride may preferably be employed.

The reaction conditions such as reaction solvent, reaction temperature, reaction time, concentration of the substrate, equivalent ratio of the reactants and the like may be appropriately selected depending on the reducing agent employed. For example, in cases where sodium borohydride is used, the desired compound may be obtained with a high yield by carrying out the reaction in an alcoholic solvent such as methanol at room temperature. In cases where the hydroxyl group is formed by the reduction step of the oxo group, β-isomer may be selectively obtained in some cases, opposite to the cases where the hydroxyl group is directly formed.

In cases where a hydroxyl group is oxidized to an oxo group, any oxidizing agent which is usually employed in oxidizing a hydroxy compound may be employed, and pyridinium chlorochromate (PCC), pyridinium dichromate (PDC), manganese dioxide, DMSO/oxalyl chloride and periodate oxidation products may preferably be employed.

The reaction conditions such as reaction solvent, reaction temperature, reaction time, concentration of the substrate, equivalent ratio of the reactants and the like may be appropriately selected depending on the oxidizing agent employed. For example, in cases where DMSO/oxalyl chloride is used, the desired compound may be obtained with a high yield by carrying out the reaction in a halogen solvent such as dichloromethane at −78° C. to 0° C.

Conversion of the hydroxy compound into the alkoxy compound or alkanoyloxy compound may be attained under the usual etherification or acylation conditions. Conversion of the compound into a salt may be attained by mixing the compound with a pharmaceutically acceptable acid in water or in a various organic solvent, and by conducting concentration to dryness, reprecipitation, recrystallization or the like.

The fact that the morphinan derivatives having the nitrogen-containing cyclic substituent, represented by Formula (I) and the pharmaceutically acceptable acid addition salts thereof are effective for functional bowel disorders may be confirmed by showing inhibitory action against transportation ability of large intestine, which ability has been increased by applying restraint stress. The inhibitory action against the increased transportation ability of large intestine may be confirmed by a reported method (Miyata K et. al., J. Pharmacol. Exp. Ther., 261, 297-303, 1992. or Kobayashi S et. al., Jpn. J. Pharmacol., 86, 281-8, 2001.), but the method is not restricted thereto.

Since the therapeutic or prophylactic agent for functional bowel disorders according to the present invention exhibits inhibitory action against the transportation ability of large intestine increased by applying restraint stress, it may be used for alleviation of various symptoms such as abnormal defecation, abdominal pain, sense of abdominal distension, abdominal discomfort, anorexia, borborygmus, vomiting, eructation, pyrosis and the like in functional bowel disorders, particularly, irritable bowel syndrome. The therapeutic or prophylactic agent for functional bowel disorders according to the present invention may be administered to mammals (e.g., mouse, rat, hamster, rabbit, cat, dog, bovine, sheep, monkey and human).

When the therapeutic or prophylactic agent for functional bowel disorders according to the present invention is administered, the compound alone may be administered, or the compound may be administered in combination with one or more substances which are used for therapy or prophylaxis of the disease and/or for alleviating or inhibiting the symptom(s). Examples of such substances include antiflatulents such as bifidobacteria, *Lactobacillus casei*, *Clostridium butyricum*, lactomin, resistant *Lactobacillus* and dried yeast; high molecular weight polymers such as polycarbophil calcium; anticholinergic drugs (parasympatholytic drugs) such as atropine sulfate, scopolamine hydrobromide, scopolamine butylbromide, N-methylscopolamine methylsulfate, anisotropine methylbromide (methyloctatropine bromide), papaverine hydrochloride, oxapium iodide, valethamate bromide, piperidolate hydrochloride, scopolia extract, butropium bromide, trepibutone, trospium chloride, etomidoline, timepidium bromide, tiquizium bromide, prifinium bromide, pipethanate ethylbromide, tiemonium iodide, methylbenactyzium bromide, propantheline bromide, dicycloverine hydrochloride (dicyclomine hydrochloride), flopropione, trihexyphenidyl hydrochloride, biperiden, profenamine, piroheptine hydrochloride, methixene hydrochloride, mazaticol hydrochloride, propiverine hydrochloride, oxybutynin hydrochloride, tolterodine hydrochloride, solifenacin succinate, darifenacin hydrobromide and KRP-197; enterokinesis regulators such as trimebutine maleate, metoclopramide, domperidone, itopride hydrochloride and mosapride citrate; cathartics such as magnesium oxide, magnesium hydroxide, magnesium sulfate, magnesium citrate, artificial carlsbad salt, carmellose sodium, castor oil, bisacodyl, sodium picosulfate, phenovalin, senna extract and sennoside; antidiarrheals such as loperamide hydrochloride, bismuth subnitrate, albumin tannate, berberine chloride, berberine sulfate, berberine tannate and natural aluminum silicate; remedies for irritable bowel syndrome such as calcium polycarbophil, mepenzolate bromide and mallotus; carminatives such as dimethylpolysiloxane; antidepressants such as nortriptyline hydrochloride, amoxapine, maprotiline hydrochloride, imipramine hydrochloride, trimipramine maleate, clomipramine hydrochloride, lofepramine hydrochloride, dosulepin hydrochloride, trazodone hydrochloride, fluvoxamine maleate, paroxetine hydrochloride hydrate, milnacipran hydrochloride, mianserin hydrochloride, setiptiline maleate and sulpiride; antianxiety drugs such as etizolam, clotiazepam, flutazolam, bromazepam, mexazolam, diazepam, cloxazolam, chlordiazepoxide, clorazepate dipotassium, medazepam, oxazolam, flutoprazepam, ethyl loflazepate, prazepam, tandospirone citrate and hydroxyzine; autonomic regulators such as tofisopam and the like. It should be noted, however, that these examples are included merely for purposes of illustration and should not be interpreted to limit the scope of the invention.

When clinically using the therapeutic or prophylactic agent for functional bowel disorders according to the present invention, the drug may be the free base or a salt thereof itself, or the drug may be in the form of a mixture with one or more additives such as vehicles, stabilizers, preservatives, buffering agents, solubilizing agents, emulsifiers, diluents and isotonic agents. The drug may be prepared by a usual method appropriately using the carrier(s) for pharmaceuticals. Examples of the formulation for administration include those for oral administration such as tablets, capsules, granules, powders and syrups; those for parenteral administration such as injection solutions, suppositories and liquids; and for topical administration such as ointments, creams and patches. These compositions may be prepared by the methods usually employed.

The therapeutic or prophylactic agent for functional bowel disorders according to the present invention preferably contains the above-described effective ingredient in a content of 0.00001 to 90% by weight, more preferably 0.0001 to 70% by weight. The dose of administration is appropriately selected depending on the symptom, age, body weight, administration method and the like, and may be, in the case of injection solution, 0.1 μg to 1 g per day per adult, and in case of a formulation for oral administration, 1 μg to 10 g per day per adult, which dose may be administered in one time or dividedly administered in several times.

The morphinan derivative having the nitrogen-containing cyclic substituent, represented by Formula (I) or the pharmaceutically acceptable acid addition salt thereof may be used as the therapeutic or prophylactic agent for functional bowel disorders. The morphinan derivative having the nitrogen-containing cyclic substituent, represented by Formula (I) or the pharmaceutically acceptable acid addition salt thereof may be used for a method for therapy or prophylaxis of a functional bowel disorder, comprising administering an effective amount of the morphinan derivative or the pharmaceutically acceptable acid addition salt thereof to a patient.

EXAMPLES

The present invention will now be described concretely referring to Reference Examples and Examples.

Reference Example 1

Synthesis of N-(17-cyclopropylmethyl-4,5α-epoxy-3,14-dihydroxy-morphinan-6β-yl)-phthalimide (Compound 1)

Compound 1

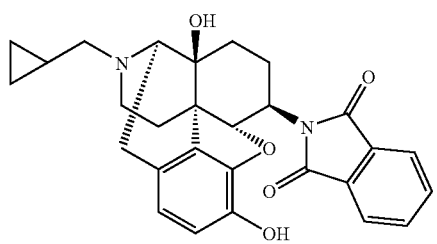

In 7 mL of DMF, 150 mg (0.44 mmol) of 6β-naltrexamine was dissolved, and 71 mg (0.48 mmol) of phthalic anhydride and 0.92 mL (0.66 mmol) of triethylamine were added, followed by stirring the resulting mixture at 140° C. for 4 hours.

The reaction solution was left to cool to room temperature, and saturated aqueous sodium hydrogen carbonate solution was added to the reaction mixture, followed by extracting the resulting mixture with ethyl acetate. Organic layers were combined and washed with water and with saturated brine. The resulting mixture was dried over anhydrous magnesium sulfate and concentrated to obtain a crude product. The obtained crude product was purified by silica gel column chromatography to obtain the captioned Compound 1 (120 mg, Yield: 58%).

$^1$H-NMR (ppm) (300 MHz, CDCl$_3$)
7.8-7.9 (2H, m), 7.7-7.8 (2H, m), 6.76 (1H, d, J=7.9 Hz), 6.63 (1H, d, J=8.2 Hz), 5.18 (1H, d, J=8.5 Hz), 4.0-4.1 (1H, m), 3.11 (1H, d, J=5.6 Hz), 3.05 (1H, d, J=18.8 Hz), 2.6-2.9 (3H, m), 2.3-2.4 (3H, m), 2.15 (1H, dt, J=12.0, 3.5 Hz), 1.4-1.7 (4H, m), 0.8-0.9 (1H, m), 0.5-0.6 (2H, m), 0.1-0.2 (2H, m)

IR (cm$^{-1}$) (KBr)
3320, 1769, 1708, 1626, 1504, 1466, 1428, 1379, 1323, 1271, 1240, 1190, 1173, 1075

Mass (EI): 472 (M$^+$)

Reference Example 2

Synthesis of N-(17-cyclopropylmethyl-4,5α-epoxy-3,10α,14-trihydroxy-morphinan-6β-yl)-phthalimide (Compound 2)

Compound 2

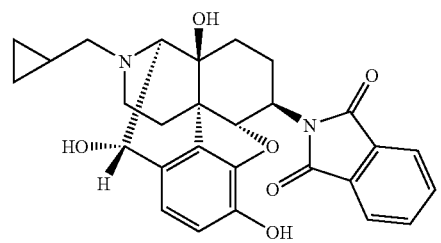

<Step 1>

Compound 3

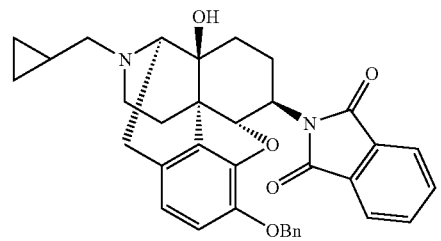

In 135 mL of DMF, 8.00 g (16.93 mmol) of the N-(17-cyclopropylmethyl-4,5α-epoxy-3,14-dihydroxy-morphinan-6β-yl)-phthalimide (Compound 1) obtained in Reference Example 1 was dissolved, and 5.15 g (37.26 mmol) of potassium carbonate was added thereto, followed by stirring the mixture to obtain a suspension. Then 3.19 g (18.65 mmol) of benzyl bromide was added, and the mixture was stirred at 40° C. for 19 hours. Then additional 1.15 g (6.72 mmol) of benzyl bromide was added, and the resulting mixture was stirred for 6 hours.

The reaction solution was allowed to cool to room temperature, and distilled water was added thereto, followed by extracting the resulting mixture with ethyl acetate. Tetrahydrofuran and 0.1N hydrochloric acid were added to the organic layer, thereby to extract the organic layer. Saturated aqueous sodium hydrogen carbonate solution was added to the obtained aqueous layer to adjust the pH of the aqueous layer to 8, and the resulting mixture was again extracted with ethyl acetate. The organic layer was washed with saturated brine, dried over anhydrous sodium sulfate, and concentrated to obtain a crude product.

The obtained crude product was subjected to slurry washing with methanol to obtain 8.11 g (Yield: 85%) of N-(3-benzyloxy-17-cyclopropylmethyl-4,5α-epoxy-14-hydroxy-morphinan-6β-yl)-phthalimide (Compound 3).

$^1$H-NMR (ppm) (400 MHz, CDCl$_3$)

0.13 (2H, m), 0.54 (2H, m), 0.86 (1H, m), 1.46-1.59 (3H, m), 1.71 (1H, m), 2.12 (1H, dt, J=4.0, 12.0 Hz), 2.33-2.39 (3H, m), 2.61-2.69 (2H, m), 2.79 (1H, dq, J=2.4, 13.2 Hz), 3.06 (1H, d, J=18.4 Hz), 3.11 (1H, d, J=5.2 Hz), 4.16 (1H, ddd, J=4.8, 8.4, 13.2 Hz), 5.09 (1H, d, J=12.0 Hz), 5.19 (1H, d, J=12.0 Hz), 5.27 (1H, d, J=8.4 Hz), 6.61 (1H, d, J=8.4 Hz), 6.76 (1H, d, J=8.4 Hz), 7.26 (1H, t, J=7.6 Hz), 7.33 (2H, t, J=7.6 Hz), 7.43 (2H, d, J=7.6 Hz), 7.70-7.73 (2H, m), 7.82-7.85 (2H, m).

IR (cm$^{-1}$) (KBr)

3434, 2928, 1773, 1712, 1612, 1500, 1453, 1377, 1333, 1281, 1241, 1190, 1172, 1148, 1108, 1089, 1059, 1042, 1017

Mass (ESI): 563 (M+1)$^+$

<Step 2>

Compound 4

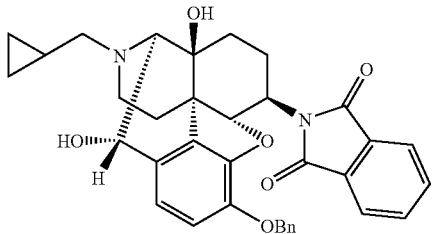

In 600 mL of acetonitrile and 32.5 mL of distilled water, 6.50 g (11.55 mmol) of the N-(3-benzyloxy-17-cyclopropylmethyl-4,5α-epoxy-14-hydroxy-morphinan-6β-yl)-phthalimide (Compound 3) was suspended, and 25.01 g (45.62 mmol) of ceric (IV) ammonium nitrate was added, followed by stirring the resulting mixture at room temperature for 24 hours.

Solid sodium hydrogen carbonate and Celite were added to the reaction solution, and the resulting mixture was stirred for 15 minutes, followed by filtration of the mixture. To the filtrate, ethyl acetate, Celite and saturated aqueous sodium hydrogen carbonate solution were added, and the resulting mixture was shaken, followed by separating the solid components together with the Celite by filtration. The obtained filtrate was separated, and the organic layer was dried over anhydrous sodium sulfate and concentrated to obtain a crude product. The obtained crude product was purified by silica gel column chromatography to obtain 2.72 g (4.71 mmol, Yield: 41%) of N-(3-benzyloxy-17-cyclopropylmethyl-4,5α-epoxy-10α,14-dihydroxy-morphinan-6β-yl)-phthalimide (Compound 4).

$^1$H-NMR (ppm) (400 MHz, CDCl$_3$)

0.13 (1H, m), 0.20 (1H, m), 0.58 (2H, m), 0.92 (1H, m), 1.47-1.52 (2H, m), 1.83-1.89 (2H, m), 2.02 (1H, dt, J=4.0, 12.4 Hz), 2.36 (1H, dt, J=5.2, 12.4 Hz), 2.52 (2H, dq, J=6.4, 12.8 Hz), 2.66 (1H, dd, J=5.2, 12.0 Hz), 2.78 (1H, dq, J=4.8, 12.8 Hz), 3.16 (1H, s), 4.17 (1H, ddd, 4.8, 8.4, 13.2 Hz), 4.99-5.00 (2H, m), 5.14 (1H, d, J=12.0 Hz), 5.22 (1H, d, J=12.0 Hz), 5.30 (1H, d, J=8.4 Hz), 6.88 (1H, d, J=8.4 Hz), 6.92 (1H, d, J=8.4 Hz), 7.28 (1H, t, J=7.2 Hz), 7.35 (2H, t, J=7.2 Hz), 7.44 (2H, d, J=7.2 Hz), 7.70-7.73 (2H, m), 7.83-7.86 (2H, m).

IR (cm$^{-1}$) (KBr)

3402, 2928, 1770, 1710, 1632, 1611, 1499, 1377, 1335, 1279, 1192, 1170, 1095, 1060, 1043, 1027

Mass (ESI): 579 (M+1)$^+$

<Step 3>

In 90 mL of tetrahydrofuran, 2.72 g (4.71 mmol) of N-(3-benzyloxy-17-cyclopropylmethyl-4,5α-epoxy-10α,14-dihydroxy-morphinan-6β-yl)-phthalimide (Compound 4) obtained in Step 2 was dissolved, and 1.36 g of 10% Pd—C (50% wet) was added thereto, followed by stirring the resulting mixture to obtain a suspension. Then 18 mL of formic acid (88% aqueous solution) was added dropwise to the mixture, and the resulting mixture was stirred at 22 to 26° C. for 15 hours.

The reaction solution was filtered to remove Pd—C, and then concentrated. To the obtained residue, tetrahydrofuran, methanol, chloroform and saturated aqueous sodium hydrogen carbonate solution were added to attain neutralization and extraction. The organic layer was dried over anhydrous sodium sulfate, and concentrated to dryness to obtain a crude product. The obtained crude product was purified by silica gel column chromatography to obtain 1.31 g (2.68 mmol, Yield: 57%) of the captioned Compound 2.

$^1$H-NMR (ppm) (500 MHz, CDCl$_3$/CD$_3$OD=7/3)

0.16 (1H, m), 0.23 (1H, m), 0.58 (2H, m), 0.95 (1H, m), 1.48-1.52 (2H, m), 1.76 (1H, m), 1.96 (1H, dt, J=3.0, 14.0 Hz), 2.07 (1H, dt, J=4.0, 12.5 Hz), 2.32 (1H, dt, J=5.5, 12.5 Hz), 2.44 (1H, dd, J=6.5, 12.5 Hz), 2.62-2.74 (3H, m), 3.10 (1H, s), 4.12 (1H, ddd, J=4.5, 8.0, 13.0 Hz), 4.98 (1H, s), 5.23 (1H, d, J=8.0 Hz), 6.82 (1H, d, J=8.0 Hz), 6.93 (1H, d, J=8.0 Hz), 7.76-7.78 (2H, m), 7.84-7.87 (2H, m).

IR (cm$^{-1}$) (KBr)

3392, 2945, 1768, 1697, 1624, 1503, 1465, 1397, 1375, 1306, 1244, 1189, 1165, 1090, 1061, 1025

Mass (ESI): 489 (M+1)$^+$

Reference Example 3

Synthesis of N-(17-cyclopropylmethyl-4,5α-epoxy-3,14-dihydroxy-10-oxo-morphinan-6β-yl)-phthalimide (Compound 5)

Compound 5

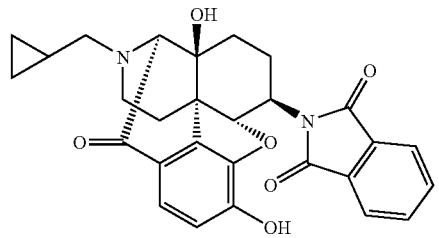

23

<Step 1>

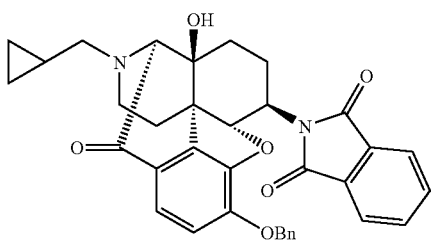

Compound 6

In 50 mL acetone, 1.51 g (2.67 mmol) of N-(3-benzyloxy-17-cyclopropylmethyl-4,5α-epoxy-14-hydroxy-morphinan-6β-yl)-phthalimide (Compound 3) obtained in Step 1 of Reference Example 2 was dissolved, and 5 mL of 1N hydrochloric acid was added thereto, followed by cooling the resulting mixture in ice. In another vessel, 274 mg (2.74 mmol) of chromium (VI) oxide was dissolved in 15 mL of 9N hydrochloric acid, and the resulting solution was added to the above-described reaction solution, followed by stirring the resulting mixture at 3° C. for 48 hours.

Isopropyl alcohol was added to the reaction solution and the resulting mixture was stirred for 30 minutes. Then saturated aqueous sodium hydrogen carbonate solution was added to the mixture to adjust the pH of the aqueous layer to 8, and the resulting mixture was extracted with chloroform. The organic layer was dried over anhydrous sodium sulfate, and concentrated to dryness to obtain a crude product. The obtained crude product was purified by silica gel column chromatography to obtain 435 mg (0.74 mmol, Yield: 28%) of N-(3-benzyloxy-17-cyclopropylmethyl-4,5α-epoxy-14-hydroxy-10-oxo-morphinan-6β-yl)-phthalimide (Compound 6).

$^1$H-NMR (ppm) (400 MHz, CDCl$_3$)

0.09 (1H, m), 0.33 (1H, m), 0.55 (2H, m), 0.93 (1H, m), 1.50-1.66 (2H, m), 1.79 (1H, m), 2.12-2.26 (2H, m), 2.54 (1H, dt, J=6.0, 13.2 Hz), 2.63-2.67 (2H, m), 2.80-2.89 (2H, m), 3.28 (1H, s), 4.16 (1H, ddd, J=4.8, 8.4, 12.8 Hz), 5.24 (1H, d, J=12.0 Hz), 5.30 (1H, d, J=12.0 Hz), 5.34 (1H, d, J=8.0 Hz), 6.93 (1H, d, J=8.4 Hz), 7.29-7.44 (6H, m), 7.72-7.74 (2H, m), 7.85-7.87 (2H, m).

Mass (ESI): 587 (M+1)$^+$

<Step 2>

In 20 mL of tetrahydrofuran, 400 mg (0.68 mmol) of N-(3-benzyloxy-17-cyclopropylmethyl-4,5α-epoxy-14-hydroxy-10-oxo-morphinan-6β-yl)-phthalimide (Compound 6) obtained in Step 1 was dissolved, and 398 mg of 10% Pd—C (50% wet) was added thereto, followed by stirring the resulting mixture to obtain a suspension. Then 427 mg of formic acid (88% aqueous solution) was added to the mixture, and the resulting mixture was stirred at 40° C. for 9.5 hours.

The reaction solution was filtered to remove Pd—C. To the filtrate, chloroform and saturated aqueous sodium hydrogen carbonate solution were added to adjust the pH of the aqueous layer to 8, and then extraction was carried out. The organic layer was dried over anhydrous sodium sulfate, and concentrated to dryness to obtain a crude product. The obtained crude product was purified by silica gel column chromatography, and the obtained concentrated residue was subjected to slurry washing with ethyl acetate to obtain 130 mg (0.27 mmol, Isolated Yield: 39%) of the captioned Compound 5.

$^1$H-NMR (ppm) (400 MHz, CDCl$_3$)

24

0.12 (1H, m), 0.33 (1H, m), 0.54 (2H, m), 0.93 (1H, m), 1.45-1.53 (2H, m), 1.63 (1H, m), 1.80 (1H, m), 2.17 (1H, dt, J=4.4, 12.4 Hz), 2.24 (1H, dd, J=7.2, 13.2 Hz), 2.54 (1H, dt, J=5.6, 12.8 Hz), 2.66 (1H, dd, J=7.2, 13.2 Hz), 2.75-2.90 (2H, m), 3.28 (1H, s), 4.07 (1H, m), 5.28 (1H, d, J=8.4 Hz), 6.94 (1H, d, J=8.4 Hz), 7.43 (1H, d, J=8.4 Hz), 7.71-7.75 (2H, m), 7.83-7.87 (2H, m).

IR (cm$^{-1}$) (KBr)

3278, 2928, 2831, 1769, 1712, 1616, 1467, 1378, 1331, 1285, 1234, 1192, 1168, 1092, 1016

Mass (ESI): 486 (M+1)$^+$

Reference Example 4

Synthesis of N-(17-cyclopropylmethyl-4,5α-epoxy-3,10β,14-trihydroxymorphinan-6β-yl)-phthalimide (Compound 7)

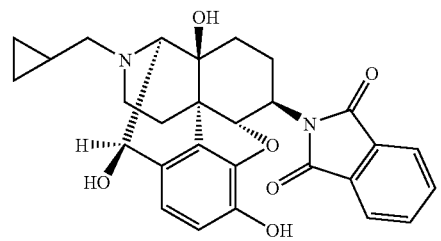

Compound 7

<Step 1>

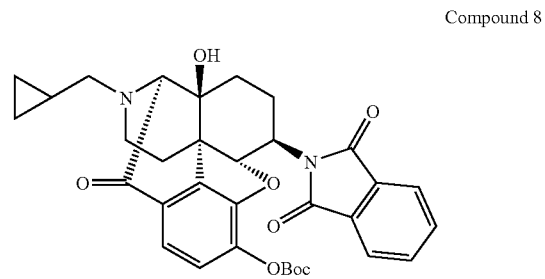

Compound 8

In 10 mL of chloroform, 210 mg (0.43 mmol) of N-(17-cyclopropylmethyl-4,5α-epoxy-3,14-dihydroxy-10-oxo-morphinan-6β-yl)-phthalimide (Compound 5) obtained by the method of Reference Example 3 was dissolved, and 100 mg (0.46 mmol) of di-t-butyldicarbonate and 5 mg (0.04 mmol) of 4-dimethylaminopyridine were added thereto, followed by stirring the resulting mixture at room temperature for 4 hours.

The reaction solution was concentrated to dryness, and the resulting product was then purified by silica gel column chromatography to obtain 152 mg (0.26 mmol, Yield: 60%) of N-(3-t-butoxycarbonyloxy-17-cyclopropylmethyl-4,5α-epoxy-14-hydroxy-10-oxo-morphinan-6β-yl)-phthalimide (Compound 8).

$^1$H-NMR (ppm) (400 MHz, CDCl$_3$)

0.11 (1H, m), 0.35 (1H, m), 0.55 (2H, m), 0.92 (1H, m), 1.46-1.57 (1H, m), 1.66 (1H, dd, J=3.2, 12.8 Hz), 1.80 (1H, m), 2.15 (1H, dt, J=4.4, 12.4 Hz), 2.25 (1H, dd, J=7.2, 12.8 Hz), 2.57 (1H, dt, J=5.6, 12.8 Hz), 2.63 (1H, dd, J=6.4, 12.8 Hz), 2.74 (1H, dq, J=2.4, 13.6 Hz), 2.87 (1H, dd, J=4.8, 12.4

Hz), 3.31 (1H, s), 4.07 (1H, m), 5.48 (1H, d, J=8.0 Hz), 7.19 (1H, d, J=8.4 Hz), 7.44 (1H, d, J=8.4 Hz), 7.71-7.75 (2H, m), 7.82-7.88 (2H, m).

IR (cm$^{-1}$) (KBr)

3375, 2974, 1777, 1712, 1681, 1620, 1383

Mass (ESI): 587 (M+1)$^+$

<Step 2>

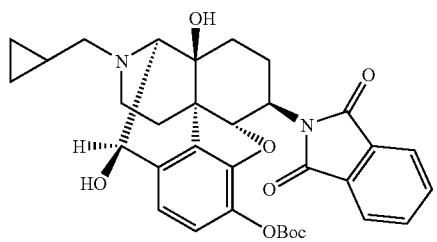

Compound 9

In 10 mL of tetrahydrofuran, 113 mg (0.19 mmol) of N-(3-t-butoxycarbonyloxy-17-cyclopropylmethyl-4,5α-epoxy-14-hydroxy-10-oxo-morphinan-6β-yl)-phthalimide (Compound 8) obtained in Step 1 was dissolved, and the reaction vessel was cooled in an ice bath. At 0° C., 4.0 mg (0.10 mmol) of sodium borohydride was added to the reaction solution. After the addition was finished, the reaction vessel was taken out of the ice bath and the temperature of the reaction mixture was returned to room temperature, followed by stirring the mixture at room temperature for 26 hours.

Ethyl acetate, distilled water and saturated aqueous sodium hydrogen carbonate solution were added to the reaction solution to carry out extraction. The organic layer was washed with distilled water, and then the resulting mixture was dried over anhydrous sodium sulfate and concentrated to dryness to obtain a crude product. The obtained crude product was purified by silica gel column chromatography to obtain 53 mg (0.09, Yield: 47%) of N-(3-t-butoxycarbonyloxy-17-cyclopropylmethyl-4,5α-epoxy-10β,14-dihydroxymorphinan-6β-yl)-phthalimide (Compound 9).

$^1$H-NMR (ppm) (400 MHz, CDCl$_3$)

0.16 (2H, m), 0.53 (2H, m), 0.90 (1H, m), 1.41-1.51 (12H, m), 1.74 (1H, m), 2.38 (1H, dt, J=5.2, 12.4 Hz), 2.55 (1H, m), 2.67 (1H, m), 2.78-2.89 (2H, m), 3.00 (1H, dd, J=6.4, 13.2 Hz), 3.21 (1H, d, J=5.2 Hz), 4.09 (1H, m), 5.06 (1H, d, J=5.2 Hz), 5.35 (1H, d, J=8.4 Hz), 7.03 (1H, d, J=8.4 Hz), 7.08 (1H, d, J=8.4 Hz), 7.70-7.72 (2H, m), 7.81-7.84 (2H, m).

Mass (ESI): 589 (M+1)$^+$

<Step 3>

In 4 mL of chloroform, 50 mg (0.07 mmol) of N-(3-t-butoxycarbonyloxy-17-cyclopropylmethyl-4,5α-epoxy-10β,14-dihydroxymorphinan-6β-yl)-phthalimide (Compound 9) obtained in Step 2 was dissolved, and 1 mL of trifluoroacetic acid was added thereto, followed by stirring the resulting mixture at room temperature for 3.5 hours.

Saturated aqueous sodium hydrogen carbonate solution was added to the reaction solution to adjust the pH of the aqueous layer to 8, and the resulting mixture was extracted with chloroform. The organic layer was dried over anhydrous sodium sulfate and concentrated to dryness to obtain a crude product. The obtained crude product was purified by preparative silica gel chromatography to obtain 13 mg (0.03 mmol, Yield: 32%) of the captioned Compound 7.

$^1$H-NMR (ppm) (400 MHz, CDCl$_3$)

0.16 (2H, m), 0.52 (2H, m), 0.91 (1H, m), 1.41-1.48 (3H, m), 1.74 (1H, m), 2.37 (1H, m), 2.60 (1H, m), 2.76-2.90 (3H, m), 3.00 (1H, dd, J=6.0, 13.2 Hz), 3.19 (1H, d, J=5.2 Hz), 4.07 (1H, m), 5.05 (1H, d, J=5.2 Hz), 5.16 (1H, d, J=8.4 Hz), 6.86 (1H, d, J=8.4 Hz), 6.96 (1H, d, J=8.4 Hz), 7.71-7.73 (2H, m), 7.83-7.86 (2H, m).

Mass (ESI): 489 (M+1)$^+$

Reference Example 5

Synthesis of N-(17-cyclopropylmethyl-4,5α-epoxy-3,14-dihydroxy-morphinan-6β-yl)-3,4,5,6-tetrahydrophthalimide•tartaric Acid Salt (Compound 10)

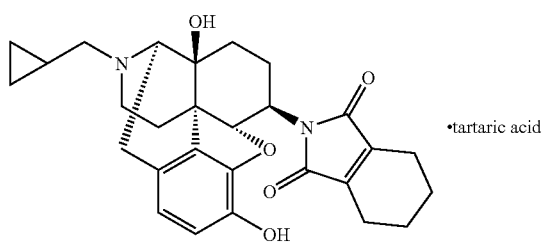

The captioned Compound 10 was obtained by the method described in Example 77 of International Publication WO 04/033457.

$^1$H-NMR (ppm) (300 MHz, CDCl$_3$)

0.12 (2H, m), 0.52 (2H, m), 0.84 (1H, m), 1.43 (3H, m), 1.65 (1H, m), 1.76 (4H, br), 2.12 (3H, td, J=12.0, 3.6 Hz), 2.26-2.38 (7H, m), 2.63 (3H, m), 3.03 (1H, d, J=18.4 Hz), 3.08 (1H, d, J=5.6 Hz), 3.83 (1H, ddd, J=13.2, 8.4, 3.6 Hz), 5.05 (1H, d, J=8.4 Hz), 6.60 (1H, d, J=8.4 Hz) (free form)

Mass (ESI): 477 (M$^+$+1)

Reference Example 6

Synthesis of 2-(17-cyclopropylmethyl-4,5α-epoxy-3,14-dihydroxy-morphinan-6β-yl)-4-fluoro-2,3-dihydro-iso-indole-1-one-methanesulfonic Acid Salt (Compound 11)

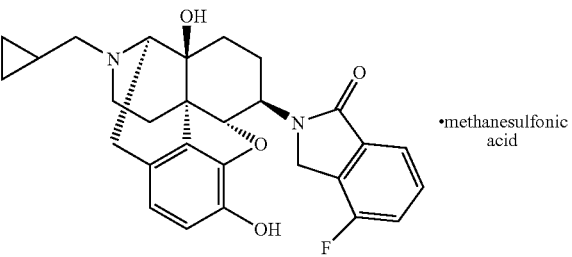

The captioned Compound 11 was obtained by the method described in Example 81 of International Publication WO 04/033457.

$^1$H-NMR (ppm) (300 MHz, CDCl$_3$)

0.14 (2H, m), 0.54 (2H, m), 0.85 (1H, m), 1.47-1.73 (4H, m), 2.13-2.29 (4H, m), 2.38 (2H, d, J=6.3 Hz), 2.59-2.67 (2H, m), 3.05 (1H, d, J=18.9 Hz), 3.10 (1H, d, J=5.4 Hz), 4.25 (1H, ddd, J=13.5, 8.1, 4.8 Hz), 4.53 (3H, m), 4.68 (1H, d, J=7.8

Hz), 6.62 (1H, d, J=8.1 Hz), 6.76 (1H, d, J=8.1 Hz), 7.22 (1H, t, J=8.7 Hz), 7.42-7.49 (1H, m), 7.64 (1H, d, J=7.8 Hz) (free form)

Mass (ESI): 477 (M$^+$+1)

Reference Example 7

Synthesis of N-(17-cyclopropylmethyl-4,5α-epoxy-3,14-dihydroxy-morphinan-6β-yl)-O-sulfonbenzimide•tartaric Acid Salt (Compound 12)

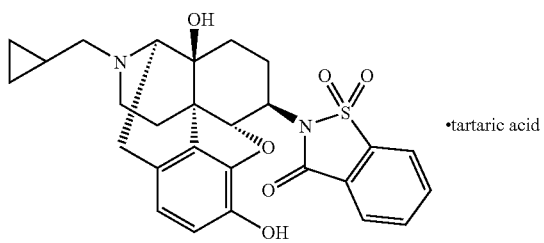

The captioned Compound 12 was obtained by the method described in Example 108 of International Publication WO 04/033457.

$^1$H-NMR (ppm) (300 MHz, CDCl$_3$)
8.06-8.08 (m, 1H), 7.82-7.97 (m, 3H), 6.80 (d, 1H, J=8.1 Hz), 6.65 (d, 1H, J=8.1 Hz), 5.28 (d, 1H, J=8.3 Hz), 3.92 (ddd, 1H, J=3.9, 8.3, 13.1 Hz), 3.11 (d, 1H, J=5.6 Hz), 3.06 (d, 1H, J=18.3 Hz), 2.78-2.87 (m, 1H), 2.60-2.70 (m, 2H), 2.32-2.39 (m, 3H), 2.13-2.20 (m, 1H), 1.46-1.76 (m, 4H), 0.82-0.88 (m, 1H), 0.52-0.57 (m, 2H), 0.12-0.15 (m, 2H) (free form)

Mass (ESI): 509 (M$^+$+1)

Reference Example 8

Synthesis of N-(17-cyclopropylmethyl-4,5α-epoxy-3,14-dihydroxy-morphinan-6β-yl)-maleimide•tartaric Acid Salt (Compound 13)

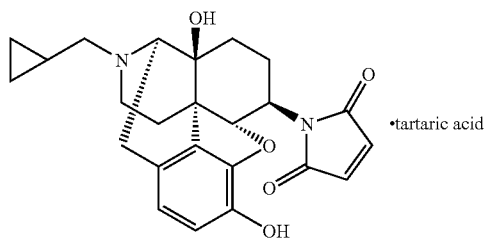

In DMF (30 mL), 800 mg (2.34 mmol) of 6β-naltrexamine was dissolved, and 252 mg (2.57 mmol) of maleic anhydride and 0.48 mL (3.50 mmol) of triethylamine were added thereto, followed by stirring the resulting mixture at room temperature for one and half hours. Thereafter, 0.53 mL (8.18 mmol) of methanesulfonic acid was added and the mixture was stirred at 120° C. for 8 hours.

The reaction solution was left to cool to room temperature, and saturated aqueous sodium hydrogen carbonate solution was added to the reaction mixture, followed by extracting the resulting mixture with ethyl acetate. Organic layers were combined and washed with water and with saturated brine. The resulting mixture was dried over anhydrous magnesium sulfate and concentrated to obtain a crude product. The obtained crude product was purified by silica gel column chromatography to obtain 141 mg (Yield: 14%) of free form of the captioned Compound 13. This product was converted to tartaric acid salt to obtain the captioned compound 13.

$^1$H-NMR (ppm) (400 MHz, CDCl$_3$)
6.70-6.75 (3H, m), 6.61 (1H, d, J=8.0 Hz), 5.02 (1H, d, J=8.3 Hz), 3.8-3.9 (1H, m), 3.08 (1H, d, J=5.6 Hz), 3.04 (1H, d, J=18.3 Hz), 2.6-2.7 (3H, m), 2.3-2.4 (3H, m), 2.12 (1H, dt, J=12.0, 3.6 Hz), 1.4-1.7 (4H, m), 0.8-0.9 (1H, m), 0.5-0.6 (2H, m), 0.1-0.2 (2H, m) (free form)

Mass (ESI): 423 (M+1)

Example 1

Effect to Rat Defecation Models Induced by Restraint Stress

A solvent or the Compound 1 was subcutaneously administered, and 15 minutes later, application of restraint stress was started. The number of feces within 60 minutes from the beginning of the application of the stress was counted and the effect was evaluated (one group consisted of 6 rats). The rats in a control group to which the restraint stress was not applied were merely moved to a new plastic cage.

In the group to which 5 w/v % xylitol solution containing 0.1 w/v % citric acid used as the solvent alone was administered, the rats to which the restraint stress was not applied defecated 1.0 feces on average within the 60 minutes, while the rats to which the restraint stress was applied defecated 6.5 feces on average, so that increase in the number of feces caused by the stress was observed.

In contrast, in the group to which Compound 1 (0.15 mg/kg) was administered and the restraint stress was applied, the number of feces was 1.0 on average, and statistically significant activity to reduce the number of feces was observed with respect to the group to which the solvent alone was administered, so that it was shown that Compound 1 is effective for functional bowel disorders.

Example 2

Compounds 10, 11, 12 and 13 were evaluated in the same manner as in Example 1. In the group to which 5 w/v % xylitol solution containing 0.1 w/v % citric acid used as the solvent alone was administered, the rats to which the restraint stress was applied defecated 7.5 feces on average within the 60 minutes. The number of feces was decreased to 0.3 on average when 0.3 mg/kg of Compound 10 was administered, decreased to 4.2 on average when 1 mg/kg of Compound 11 was administered, decreased to 3.7 on average when 0.3 mg/kg of Compound 12 was administered, and decreased to 4.1 on average when 10 mg/kg of Compound 13 was administered. Significant activity to reduce the number of feces was observed with all of these test substances with respect to the group to which the solvent alone was administered, so that it was shown that these compounds are effective for functional bowel disorders.

The invention claimed is:

1. A method for therapy of a diarrhea-predominant irritable bowel syndrome, comprising administering an effective amount of a morphinan derivative having the nitrogen-containing cyclic substituent of Formula (I):

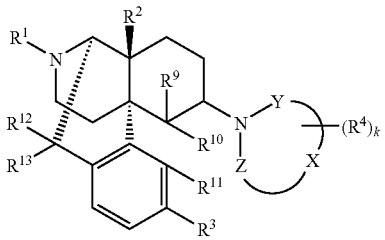

(I)

wherein R¹ is $C_4$-$C_7$ cycloalkylalkyl;
R² and R³ are independently hydroxy;
Y and Z independently represent —C(=O)—;
—X— represents $C_2$ alkenylene;
k is 2;
R⁴s are substituents in the number of k on the nitrogen-containing ring, wherein two R⁴s bound to adjacent carbon atoms, respectively, together form unsubstituted benzo, or cyclohexeno;
R⁹ is hydrogen;
R¹⁰ and R¹¹ are bound to form —O—:
R¹² and R¹³ are hydrogen; and
the Formula (I) includes (+), (−) and (±) isomers,
or a pharmaceutically acceptable acid addition salt thereof.

* * * * *